US008703802B2

(12) United States Patent
Dull et al.

(10) Patent No.: US 8,703,802 B2
(45) Date of Patent: Apr. 22, 2014

(54) PROCESS FOR THE PREPARATION OF ARYL SUBSTITUTED OLEFINIC AMINES

(75) Inventors: Gary Maurice Dull, Winston-Salem, NC (US); John Genus, Winston-Salem, NC (US); Tommi Ratilainen, Sodertalje (SE); Per Olof Ryberg, Sodertalje (SE); Janna Hellström, Macclesfield (GB); Niklas Wahlström, Macclesfield (GB); Thomas Wännman, Sodertalje (SE)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 13/697,807

(22) PCT Filed: May 19, 2011

(86) PCT No.: PCT/SE2011/050630
§ 371 (c)(1),
(2), (4) Date: May 9, 2013

(87) PCT Pub. No.: WO2011/146009
PCT Pub. Date: Nov. 24, 2011

(65) Prior Publication Data
US 2013/0225827 A1 Aug. 29, 2013

Related U.S. Application Data

(60) Provisional application No. 61/346,504, filed on May 20, 2010.

(51) Int. Cl.
| A01N 43/40 | (2006.01) |
| A61K 31/44 | (2006.01) |
| A61K 31/435 | (2006.01) |
| C07D 213/62 | (2006.01) |
| C07D 213/78 | (2006.01) |

(52) U.S. Cl.
USPC ........... 514/347; 514/345; 514/277; 546/300; 546/290; 564/509

(58) Field of Classification Search
USPC ....................................................... 546/130
See application file for complete search history.

(56) References Cited

U.S. PATENT DOCUMENTS

| 4,192,946 A | 3/1980 | Clauson-Kaus et al. |
| 4,487,607 A | 12/1984 | Rose et al. |
| 4,582,823 A | 4/1986 | Heffner et al. |
| 4,922,901 A | 5/1990 | Brooks et al. |
| 5,013,753 A | 5/1991 | Casagrande et al. |
| 5,073,547 A | 12/1991 | Casagrande et al. |
| 5,187,166 A | 2/1993 | Kikuchi et al. |
| 5,212,188 A | 5/1993 | Caldwell et al. |
| 5,583,140 A | 12/1996 | Bencherif et al. |
| 5,597,919 A | 1/1997 | Dull et al. |
| 5,604,231 A | 2/1997 | Smith |
| 5,616,707 A | 4/1997 | Crooks et al. |
| 5,616,716 A | 4/1997 | Dull et al. |
| 5,663,356 A | 9/1997 | Ruecroft et al. |
| 5,672,601 A | 9/1997 | Cignarella et al. |
| 5,726,316 A | 3/1998 | Crooks |
| 5,811,442 A | 9/1998 | Ben et al. |
| 5,852,041 A | 12/1998 | Cosford et al. |
| 5,861,423 A | 1/1999 | Caldwell |
| 6,232,316 B1 | 5/2001 | Dull et al. |
| 6,274,606 B1 | 8/2001 | Caldwell et al. |
| 6,337,351 B1 | 1/2002 | Dull et al. |
| 6,432,954 B1 | 8/2002 | Dull et al. |
| 6,492,399 B1 | 12/2002 | Dull et al. |
| 6,599,897 B1 | 7/2003 | Brown |
| 6,603,011 B1 | 8/2003 | Caldwell et al. |
| 6,632,823 B1 | 10/2003 | Vernier et al. |
| 6,743,812 B1 | 6/2004 | Dull |
| 6,958,399 B2 | 10/2005 | Caldwell et al. |
| 6,979,695 B2 | 12/2005 | Caldwell et al. |
| 7,459,469 B2 | 12/2008 | Munoz et al. |
| 2002/0016460 A1 | 2/2002 | Snow et al. |
| 2002/0052497 A1 | 5/2002 | Caldwell et al. |
| 2003/0069272 A1 | 4/2003 | Yerxa et al. |
| 2003/0125345 A1 | 7/2003 | Caldwell et al. |
| 2004/0044023 A1 | 3/2004 | Cantillon et al. |
| 2004/0067974 A1 | 4/2004 | Czollner et al. |
| 2005/0203130 A1 | 9/2005 | Buntinx |
| 2006/0024358 A1 | 2/2006 | Santini et al. |
| 2006/0062838 A1 | 3/2006 | Dipierro et al. |

(Continued)

FOREIGN PATENT DOCUMENTS

| EP | 0297858 | 1/1989 |
| EP | 0516409 | 12/1992 |

(Continued)

OTHER PUBLICATIONS

Pomerleau, O.F., et al., "The Effects of Cigarette Smoking on Pain and Anxiety," *Addictive Behaviors*, 9: 265-271 (1984).
Pullen, R.D., et al. "Transdermal Nicotine for Active Ulcerative Colitis," *New England J. Med.*, 330(12): 811-815 (1994).
Rapier, C., et al., "Stereoselective Nicotine-Induced Release of Dopamine from Striatal Synaptosomes: Concentration Dependence and Repetitive Stimulation," *J. Neurochem.*, 50(4): 1123-1130 (1988).
Rowell, P.P. and D.L. Winkler, "Nicotinic Stimulation of [$^3$H] Acetylcholine Release from Mouse Cerebral Cortical Synaptosomes," *J. Neurochem.*, 43(6): 1593-1598 (1984).
Sanberg, P.R., et al., "Nicotine Potentiation of Haloperidol-Induced Catalepsy: Striatal Mechanisms," *Pharmacol. Biochem. & Behavior*, 46: 303-307 (1993).
Sandor, N.T., et al. "Effect of nicotine on dopaminergic-cholinergic interaction in the striatum," *Brain Res.*, 567: 313-316 (1991).
Schmitt, J.D., and M. Bencherif, "Chapter 5. Targeting Nicotinic Acetylcholine Receptors: Advances in Molecular Design and Therapies," *Ann. Rep. Med. Chem.*, 35: 41-51 (2000).
Sjak-Shie, N.N. and E.M. Meyer, "Effects of chronic nicotine and pilocarpine administration on neocortocal neuronal density and [$^3$H]GABA uptake in nucleus basalis lesioned rats," *Brain Res.*, 624: 295-298 (1993).

(Continued)

*Primary Examiner* — John Mabry
*Assistant Examiner* — Daniel Carcanague
(74) *Attorney, Agent, or Firm* — Amy H. Fix

(57) ABSTRACT

An improved process for the preparation of aryl substituted olefinic amines such as (2S)-(4E)-N-methyl-5-[3-(5-isopropoxypyridin)yl]-4-penten-2-amine and (2S)-(4E)-N-methyl-5-[3-(5-methoxypyridin)yl]-4-penten-2-amine and new intermediates used in said process.

15 Claims, No Drawings

(56) References Cited

U.S. PATENT DOCUMENTS

| | | |
|---|---|---|
| 2006/0122237 A1 | 6/2006 | Munoz et al. |
| 2006/0122238 A1 | 6/2006 | Dull et al. |
| 2006/0159768 A1 | 7/2006 | Brown |
| 2007/0265314 A1 | 11/2007 | Dull et al. |
| 2008/0085888 A1 | 4/2008 | Breining et al. |
| 2008/0249142 A1 | 10/2008 | Dull et al. |
| 2009/0062321 A1 | 3/2009 | Munoz et al. |

FOREIGN PATENT DOCUMENTS

| | | |
|---|---|---|
| GB | 2295387 | 5/1996 |
| JP | 70012732 | 11/1967 |
| WO | WO-92/12122 | 7/1992 |
| WO | WO-94/08992 | 4/1994 |
| WO | WO-95/34555 | 12/1995 |
| WO | WO-96/31475 | 10/1996 |
| WO | WO-96/40682 | 12/1996 |
| WO | WO-97/40011 | 10/1997 |
| WO | WO-99/21834 | 5/1999 |
| WO | WO-99/65876 | 12/1999 |
| WO | WO-00/07600 | 2/2000 |
| WO | WO-00/45846 | 8/2000 |
| WO | WO-00/75110 | 12/2000 |
| WO | WO-01/17943 | 3/2001 |
| WO | WO-01/78735 | 10/2001 |
| WO | WO-02/05801 | 1/2002 |
| WO | WO-02/078639 | 10/2002 |
| WO | WO-03/051302 | 6/2003 |
| WO | WO-03/082205 | 10/2003 |
| WO | WO-2004/031151 | 4/2004 |
| WO | WO-2005/072742 | 8/2005 |
| WO | WO-2005/105729 | 11/2005 |
| WO | WO-2006/053039 | 5/2006 |
| WO | WO-2006/053082 | 5/2006 |
| WO | WO-2006/114400 | 11/2006 |
| WO | WO-2007/134034 | 11/2007 |
| WO | WO-2007/134038 | 11/2007 |
| WO | WO-2007/147014 | 12/2007 |
| WO | WO-2008/034041 | 3/2008 |
| WO | WO-2008/073942 | 6/2008 |

OTHER PUBLICATIONS

Toth, E., et al., "Effect of Nicotine of Extracellular Levels of Neurotransmitters Assessed by Microdialysis in Various Brain Regions: Role of Glutamic Acid," *Neurochem. Res.*, 17(3): 265-270 (1992).

Tripathi, H.L., et al., "Nicotine-Induced Antinociception of Rats and Mice: Correlation with Nicotine Brain Levels," *J. Pharmacol. Exp. Ther.*, 221(1): 91-96 (1982).

Vizi, E.S., "Acetylcholine release from guinea-pig ileum by parasympathetic ganglion stimulants and gastrin-like polypeptides," *Br. J. Pharmac.*, 47: 765-777 (1973).

Wagner, B., et al., "Does Smoking Reduce the Risk of Neuroleptic Parkinsonoids?," *Pharmacopsychiat.*, 21: 302-303 (1988).

Williams, M., et al., "Neuronal Nicotinic Acetylcholine Receptors," *DN&P*, 7(4): 205-223 (1994).

Brioni, J.D., et al., "The Pharmacology of (−)-Nicotine and Novel Cholinergic Channel Modulators," *Adv. Pharmacol.*, 37: 153-214 (1997).

Cheng, Yung-Chi, and W.H. Prusoff, "Relationship Between the Inhibition Constant ($K_I$) and the Concentration of Inhibitor which Causes 50 Per Cent inhibition ($I_{50}$) of an Enzymatic Reaction," *Biochem. Pharmacol.*, 22(23): 3099-3108 (1973).

Chiari, A., et al., "Sex Differences in Cholinergic Analgesia I: A Supplemental Nicotinic Mechanism in Normal Females," *Anesthesiology*, 91(5): 1447-1454 (1999).

Damaj, M.I., et al., "Analgesic Activity of Metanicotine, A Selective Nicotinic Agonist," *Society for Neuroscience*, 23: 669 Abstract 266.9 (1997).

Damaj, M.I., et al., "Antinociceptive and Pharmacological Effects of Metanicotine, a Selective Nicotinic Agonist," *J. Pharmacol. Exp. Ther.*, 291(1): 390-398 (1999).

Decina, P., et al., "Cigarette Smoking and Neuroleptic-Induced Parkinsonism," *Biol. Psychiatry*, 28(6): 502-508 (1990).

Gibson, S. et al., "Principal Components Describing Biological Activities and Molecular Diversity of Heterocyclic Aromatic Ring Fragments," *J. Med. Chem.*, 39: 4065-4072 (1996).

Hall, G.H. and D.M. Turner, "Effects of Nicotine on the Release of $^3$H-Noradrenaline from the Hypothalamus," *Biochemical Pharmacology*, 21: 1829-1838 (1972).

Hamon, M., "Neuropharmacology of anxiety: perspectives and prospects," *TiPS*, 15: 36-39 (1994).

Harsing, Jr., L.G., et al., "Dopamine Efflux from Striatum After Chronic Nicotine: Evidence for Autoreceptor Desensitization," *J. Neurochem.*, 59: 48-54 (1992).

Hery, F., et al., "Control of the Release of Newly Synthetized $^3$H-5-Hydroxytryptamine by Nicotinic and Muscarinic Receptors in Rat Hypothalamic Slices," *Naunyn-Schmiedeberg's Arch. Pharmacol.*, 296: 91-97 (1977).

Holladay, M.W., et al., "Neuronal Nicotinic Acetylcholine Receptors as Targets for Drug Discovery," *J. Med. Chem.*, 40(26): 4169-4194 (1997).

Arneric, S., et al., "Cholinergic channel modulators as a novel therapeutic strategy for Alzheimer's disease," Exp. Opin. Invest. Drugs 5(1): 79-100 (1996).

Arneric, S., et al., "Preclinical Pharmacology of ABT-418: A Prototypical Cholinergic Channel Activator for the Potential Treatment of Alzheimer's Disease," *CNS Drug Rev.* 1(1): 1-26 (1995).

Bannon, A. W., et al., "Broad-Spectrum, Non-Opioid Analgesic Activity by Selective Modulation of Neuronal Nicotinic Acetylcholine Receptors," *Science*, 279: 77-80 (1998).

Bencherif, M., and J. D. Schmitt, "Targeting Neuronal Nicotinic Receptors: a Path to New Therapies," *Current Drug Targets*, 1(4): 349-357 (2002).

Bencherif, M., et al., "RJR-2403: A Nicotinic Agonist with CNS Selectivity I: In Vitro Characterization," *J. Pharmacol. Exper. Therapeutics*, 279(3): 1413-1421 (1996).

Levin, E.D., et al., "Nicotine-haloperidol interactions and cognitive performance in schizophrenics," Neuropsychopharmacol. 15: 429-436 (1996).

Paulder et al., "1,2,4-Triazines. III. A convenient synthesis of 1,2,4-triazines and their covalent hydration," J Heterocyclic Chem (1970) 7:767-771.

Rondahl, "Synthetic analogues of nicotine VI1,2. Nicotine substituted in the 5-position," Acta Pharmaceutica Suecica (1977) 14(2):113-118.

Taylor et al., "Intramolecular diels-alder reactions of 1,2,4-triazines. A general synthesis of furo[2,3-]pyridines, 2,3-dihydropyrano[2,3-]pyridines, and pyrrolo[2,3-]pyridines," Tetrahedron (1987) 43(21):5145-5158.

Viaud et al., "Synthesis of 6-substituted 2-phenyloxazolo-[4,5-b]pyridines," Heterocycles (1995) 41(12):2799-2809.

Yoshikawa et al., "Synthesis of 3-pyridinols. II. Reaction of 4-methyloxazole with dienophiles," Chem Pharm Bull (1965) 13(7):873-878.

Bibliographic printout from DIALOG research company (corresponding to Japanese Patent No. 70012732), 1970.

Cai et al., "5-(N-Oxyaza-7-substituted-1,4-dihydroquinoxaline-2,3-diones: Novel, Systemically Active and Broad Spectrum An," J Med Chem (1997) 40(22):3679-3686.

Comins et al., "Lithiation of Methoxypyridines Directed by beta-Amino Alkoxides," (1990) J Org Chem 91(5):69-73.

Dallacker et al., "1.3-Dioxolohetarene, 3 [1] Darstellung und Reaktionen von Pyrido[3.4-d][1.3]dioxolen," Naturforsch (1979) 34b:1729-1736.

Dubey et al., "Synthesis & Spectra of 2-Alkyl—& 6-Bromo-2-alkyl-1H-imidazo[b]pyridines," Indian J Chem (1978) 16B (6):531-533.

Dwoskin et al., "Recent developments in neuronal nicotinic acetylcholine receptor antagonists," Exp Opin Ther Patents (2000) 10(10):1561-1581.

Frank et al., "Palladium-Catalyzed Vinylic Substitution Reactions with Heterocyclic Bromides," J Org Chem (1978) 43 (15):2947-2949.

(56) References Cited

OTHER PUBLICATIONS

Frissen et al., "Ring-Transformations of Pyrimidines by Intramolecular Diels-Alder Reactions, Sythesis of Annelated Pyridines," Tetrahedron (1989) 45(3):803-812.
Greco et al., "Synthese of Some Substituted Pyridylsydnones," J Heterocyclic Chem (1970) 7:761-766.
Hayes et al., "Elimination of Dihydrogen from Collision-activated Alkoxide Negative Ions in the Gas Phase. An Abinition and Isotope Effect Study," J Chem Soc Chem Commun (1984) 21:1431-1432.
Hertog et al., "The Reactivity of Bromine Atoms in Brominated Pyridines," Red Tray Chim Pays-Bas (1948) 67 (718):377-379.
Buccafusco "Neuronal nicotinic receptor subtypes: defining therapeutic targets," Molecular Interventions (2004) 4 (5):285-295.
Geerts, "Ispronicline Targacept," Current Opinion in Investigational Drugs (2006) 7(1):60-69.
Haberman, "Nicotinic receptor agonists for treating diseases of cognitive dysfunction," Spectrum (2007) pp. 11-1 to 11-19.
Gould, "Salt selection for basic drugs" International Journal of Pharmaceutics (1986) 33:201-217.
Berge et al., "Pharmaceutical Salts," (1977) J Pharma Sci 66(1):1-19.
Letchworth et al., "TC-1734: an orally active neuronal nicotinic receptor modulator with long-lasting cognitive effects, anti-depressant effects, and neuroprotective activity," Society for Neuroscience (2003) Abstract.
Loffer et al., "[Uber die bildung des i-nicotins aus N-methyl-b-pyridyl-butyl-amin (dihydrometanicotin)]," Chem Ber (1909) 42:3431-3438.
Michael et al., "Synthesis of functionalized cyclopentanes, cyclohexanes and cycloheptanes by a silicon-induced domino reaction," Liebigs Ann (1996) 11:1811-1821.
Morisawa et al., "Modification at 5-position of 4-deoxypyridoxol and alpha4-norpyridoxol," Agr Biol Chem (1975) 39 (6):1275-1281.
de Costa et al., "Synthesis and biological evaluation of conformationally restricted 2-(1-pyrrolidinyl)-N-[2-(3,4-dichlorophenypethy1]-N-methylethylenediamines as sigma receptor ligands. 1. Pyrrolidine, piperidine, homopiperidine, and tetrahydroisoquinoline classes," J med Chem (1992) 35(23):4334-4343.
Koller et al., "The Preparation of Substituted Hydroxyphenyl-pyridyl-ethanols and -Hydroxyphenyl—methylpyridineethanols by the Condensation of 2-, 3-, or 4-Picolyllithium with Select Hydroxy-benzaldehydes and 4-Hydroxyacetophenone," Synthetic Communications (1995) 25(19):2963-2974.
Acheson et al., "Transformations involving the Pyrrolidine Ring of Nicotine," J Chem Soc (1980) 1:579-585.
Ashimori et al., "Novel 1, 4-Dihydropyride Calcium Antagonists. I. Synthesis and Hypotensive Activity of 4-(Substittuted Pyridyl)-1,4-dihydropyridine Derivatives," Chem. Pharm Bull (1990) 38(9):2446-2458.
Batkowski, Rocz Chem (1967) 41:729-741.
Borch, "Reductive Amination with Sodium Cyanoborohydride: N, N-Dimethylcyclohexyl," Org Syn (1974) 52:124-127.
Bastin et al, "Salt Selection and Optimization for Pharmaceutical New Chemical Entities," Organic Process Research and Development, 2000; 4(5):427-435.
Ichikawa et al., "Atypical antipsychotic drugs, quetiapine, iloperidone, and melperone, preferentially increase dopamine and acetylcholine release in rat medial prefrontal cortex: role of 5-HT1A receptor agonism," Brain Research (2002) 956:349-357.
Shoemaker, et al., "Quetiapine produces a prolonged reversal of the sensorimotor gating-disruptive effects of basolateral amygdala lesions in rats," Behavioral Neuroscience (2003) 117(1):136-143.
Malek et al., "Palladium-Catalyzed Synthesis of Cinnamylamines," J Org Chem (1982) 47:5395-5397.

PROCESS FOR THE PREPARATION OF ARYL SUBSTITUTED OLEFINIC AMINES

REFERENCE TO RELATED APPLICATIONS

This application is a National Phase filing of PCT Application PCT/SE2011/050630 filed May 19, 2011 which claims the benefit of U.S. Provisional Application No. 61/346,504 filed May 20, 2010.

FIELD OF THE INVENTION

The present invention relates to improved processes for the preparation of aryl substituted olefinic amines such as (2S)-(4E)-N-methyl-5-[3-(5-isopropoxypyridin)yl]-4-penten-2-amine and (2S)-(4E)-N-methyl-5-[3-(5-methoxypyridin)yl]-4-penten-2-amine and to new intermediates used in said processes.

BACKGROUND

Aryl substituted olefinic amines are useful as neuronal nicotinic receptor agonists, especially as alpha-4/beta-2 ($\alpha 4\beta 2$)-neuronal nicotinic receptor agonists. These compounds are contemplated to be useful in treatment and prophylaxis of disorders related to the central nervous system (CNS). Examples of such disorders are, for example Alzheimer's Disease, pre-senile dementia (early onset Alzheimer's Disease), dementia of the Alzheimer's type, attention deficit disorder, including attention deficit hyperactivity disorder, schizophrenia, mild cognitive impairment, age associated memory impairment, cognitive dysfunction in schizophrenia and pain.

The preparation of aryl substituted olefinic amines has been described in U.S. Pat. Nos. 6,603,011, 6,958,399, 6,274,606, 6,979,695, 6,432,954, and PCTs WO2006/053039 and WO2006/053082, each of which is incorporated herein by reference in its entirety.

The preparation of p-hydroxybenzoate salt of (2S)-(4E)-N-methyl-5-[3-(5-isopropoxypyridin)yl]-4-penten-2-amine is described in WO2006/053082, which is incorporated herein by reference in its entirety.

Further salts of p-hydroxybenzoate salt of (2S)-(4E)-N-methyl-5-[3-(5-isopropoxypyridin)yl]-4-penten-2-amine are described in WO2007/134038 and U.S. Pat. No. 6,432,954, which is incorporated herein by reference in its entirety.

Polymorphic forms of p-hydroxybenzoate salt of (2S)-(4E)-N-methyl-5-[3-(5-isopropoxypyridin)yl]-4-penten-2-amine are described in WO2007/134034, which is incorporated herein by reference in its entirety.

DESCRIPTION OF THE INVENTION

Described herein is a new process for manufacturing aryl substituted olefinic amines such as (2S)-(4E)-N-methyl-5-[3-(5-isopropoxypyridin)yl]-4-penten-2-amine and (2S)-(4E)-N-methyl-5-[3-(5-methoxypyridin)yl]-4-penten-2-amine.

It has now been found that several process steps can be improved thereby increasing the selectivity, the conversion and the yields of the several steps and the yield of the overall process. Also, the reaction times of several steps are shortened and the level of impurities decreased.

Further, the new process is more suited for large scale manufacturing of aryl substituted olefinic amines such as (2S)-(4E)-N-methyl-5-[3-(5-isopropoxypyridin)yl]-4-penten-2-amine and (2S)-(4E)-N-methyl-5-[3-(5-methoxypyridin)yl]-4-penten-2-amine.

The new process is contemplated to be more scalable and reproducible and to be economically and environmentally more favourable.

Also described herein is a process for the preparation of 4-penten-2-ol comprising adding vinylmagnesium chloride to a mixture of copper(I) chloride and lithium chloride, followed by the addition of propylene oxide, in a suitable solvent.

In one aspect the amounts used are 0.01 mole-equivalent copper(I) chloride and 0.02 mole-equivalent lithium chloride relative to propylene oxide.

In another aspect the amount of vinylmagnesium chloride used is less than or equal to 1.0 mole-equivalent relative to propylene oxide.

Described herein is a process for the preparation of N-(tert-butoxycarbonyl)-N-methyl-4-penten-2-amine comprising preparing of 4-penten-2-ol, adding 4-penten-2-ol to a solution of 1.0 mole-equivalent (relative to propylene oxide) of p-toluenesulfonyl chloride in tetrahydrofuran, adding the resulting 4-penten-2-yl p-toluenesulfonate in tetrahydrofuran solution, to 40% aqueous methylamine, combining the resulting N-methyl-4-penten-2-amine solution with a mixture of di-tert-butyl dicarbonate in methyl tert-butyl ether, and adding N,N-dimethylethanediamine to the reaction mixture of N-methyl-4-penten-2-amine to N-(tert-butoxycarbonyl)-N-methyl-4-penten-2-amine.

Also described herein is a process for the preparation of N-methyl-4-penten-2-amine di-benzoyl-L-(−)-tartaric acid comprising adding a solution of (L)-(−)-benzoyl-tartaric acid (0.5 mole-equivalent relative to N-methyl-4-penten-2-amine) to a solution of N-methyl-4-penten-2-amine in an organic solvent.

Described herein is a process for the preparation of aryl substituted olefinic amines such as (2S)-(4E)-N-methyl-5-[3-(5-isopropoxypyridin)yl]-4-penten-2-amine or (2S)-(4E)-N-methyl-5-[3-(5-methoxypyridin)yl]-4-penten-2-amine comprising: mixing (2S)-N-(tert-butoxycarbonyl)-N-methyl-4-penten-2-amine (1 mole-equivalent) and 5-bromo-3-alkoxypyridine (1.1 mole-equivalents) with a palladium source (0.01 mole-equivalents), a phosphine ligand (0.24 mole-equivalents) and a base (1.5 mole-equivalents) in a suitable organic solvent under an atmosphere of nitrogen, adding water and heating the mixture to 90° C. for 15 to 25 h or until the appropriate level of conversion has been achieved, cooling the mixture and adding water and an acid, followed by stirring at 0-70° C. for 3 to 8 h, separating the organic solvent and the acidic aqueous phase followed by washing the aqueous phase with an organic solvent, adjusting the pH in the aqueous phase by the addition of a base, and extracting the product into the organic phase followed by separation of the organic phase, and optionally treating the organic phase with a metal scavenger or charcoal.

A further process described herein is for the preparation of N-methyl-5-[3-(5-isopropoxypyridin)yl]-4-penten-2-amine according to the procedures described herein where the catalyst and toluene are reused in a series of consecutive batches, whereby the palladium containing toluene phase is kept in the reactor and put under an atmosphere of nitrogen and the cycle is repeated by the addition of N-(tert-butoxycarbonyl)-N-methyl-4-penten-2-amine (1 mole-equivalent) and 5-bromo-3-alkoxoxypyridine (1.1 mole-equivalents) and base (1.5 mole-equivalents) followed by steps b) to e) or optionally g).

In one aspect of the processes described, an acid used is hydrochloric acid.

In another aspect of the processes described, the base used is an amine.

In another aspect of the processes described, the phosphine ligand is a mono or bis phosphine.

In another aspect of the processes described the palladium source is a Pd(II) complex or a Pd(0) complex.

Described herein is the intermediate compound N-methyl-4-penten-2-amine hemi-di-benzoyl-L-(−)-tartaric acid salt.

One aspect of the invention relates to a process for the preparation of (2S)-N-(tert-butoxycarbonyl)-N-methyl-4-penten-2-amine using steps 1 to 4a as shown in Scheme 1.

Scheme 1

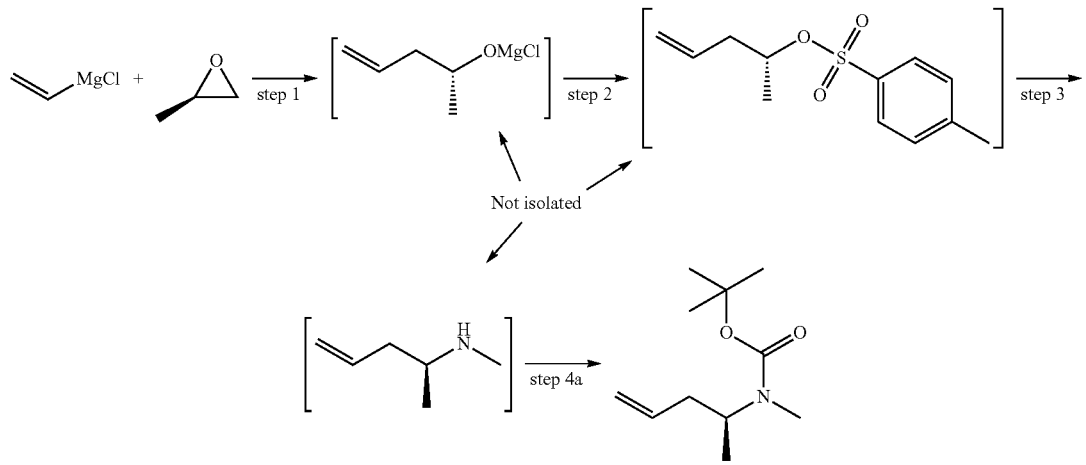

Step 1 of Scheme 1:

One embodiment of the invention relates to a process for the preparation of 4-penten-2-ol by adding vinylmagnesium chloride to a mixture of copper(I) chloride and lithium chloride, prior to the addition of propylene oxide, in a suitable solvent.

Another embodiment relates to process step 1, whereby the amounts used are 0.01 mole-equivalent copper(I) chloride and 0.02 mole-equivalent lithium chloride relative to propylene oxide.

In yet another embodiment the amount of vinylmagnesium chloride is 1.0 mole-equivalent relative to propylene oxide.

The Grignard reaction has been modified by the exchange of copper(II) iodide with a mixture of copper(I) chloride and lithium chloride.

The amount of copper used has been reduced to a catalytic amount, from 0.15 mole-equivalent relative to propylene oxide in the previous to 0.01 mole-equivalent copper(I) chloride and 0.02 mole-equivalent lithium chloride.

The reduction of the amount of copper(I) chloride results in less impurities generated during the reaction steps and less waste products thus making this process step more environmentally friendly, and more suitable for manufacturing by reducing the number of operations in the process and removing a cumbersome filtration.

The addition of the co-catalyst, lithium chloride, increases the conversion and selectivity of this process step.

Further, the amount of vinylmagnesium chloride used is decreased from 1.50 mole-equivalent to 1.02 mole-equivalent relative to propylene oxide. As a consequence of this, less p-toluenesulfonyl chloride is needed in step 2.

Another advantage is that the reaction mixture can be used directly in the next step without using the work-up procedure described in the previous process such as filtering off the copper salt.

Non-limiting examples of suitable ether solvents may be selected from the group comprising tetrahydrofuran, 2-methyltetrahydrofuran, methyl tert-butyl ether and 1,4-dioxane.

In one embodiment the solvent is tetrahydrofuran.

Non-limiting examples of other copper salts that may be used are copper(I) cyanide, copper(I) cyanide in combination with lithium chloride, copper(I) cyanide in combination with lithium bromide, copper bromide, lithium 2-thienylcyanocuprate and copper (I) bromide-dimethyl sulfide.

In yet a further aspect the temperature in said process step 1 is from −20° C. to 10° C. Typically, the reaction temperature is around 0° C. before propylene oxide is added and the temperature decreased to −15° C.

In one embodiment the enantiomer R-propylene oxide is used to prepare 4-penten-2(R)-ol. In another embodiment the enantiomer S-propylene oxide is used to prepare 4-penten-2(S)-ol.

Step 2 of Scheme 1:

One aspect of the invention relates to a process for the preparation of 4-penten-2-yl p-toluenesulfonate by adding the magnesium salt of 4-penten-2-ol to a solution of p-toluenesulfonyl chloride in tetrahydrofuran, whereby the amount of p-toluenesulfonyl chloride is 1.0 mole-equivalent relative to propylene oxide.

In one embodiment the reaction mixture obtained is subsequently transferred to a mixture of water and methyl tert-butyl ether followed by the addition of an acid, such as hydrochloric acid, until acidic pH is obtained, whereafter the phases are separated and the organic phase is washed and distilled.

The amount of p-toluenesulfonyl chloride used is decreased from 1.1 mole-equivalent to 1.0 mole-equivalent relative to propylene oxide. Also, the solvent is changed from pyridine and dried dichloromethane of the previous process to tetrahydrofuran.

The filtration previously needed to remove copper salts is not required due to the lower amount of copper used in the previous step.

The work-up method is changed from repeatedly washing the organic phase and drying with sodium sulfate to a partitioning of the mixture between aqueous acid and methyl tert-butyl ether (including one additional extraction of the aqueous phase with methyl tert-butyl ether), followed by washing with brine and distillation of the methyl tert-butyl ether.

The overall preparation time has become shorter. Also, the use of sodium sulfate is not suitable for large scale manufacturing.

In a further embodiment, process step 2 is performed at a temperature of from −5 to 30° C.

Non-limiting examples of suitable ether solvents may be selected from the group comprising tetrahydrofuran, 2-methyltetrahydrofuran and 1,4-dioxane.

In one embodiment, the solvent is tetrahydrofuran.

In a further embodiment, the enantiomer 4-penten-2(R)-ol is used to prepare (R)-4-penten-2-yl p-toluenesulfonate. In yet another embodiment 4-penten-2(S)-ol is used to prepare (S)-4-penten-2-yl p-toluenesulfonate.

Step 3 of Scheme 1:

One aspect relates to a process for the preparation of N-methyl-4-penten-2-amine by adding 4-penten-2-yl p-toluenesulfonate in tetrahydrofuran, over time, to a refluxing solution of 40% aqueous solution of methylamine (7.3 mole-equivalent relative to propylene oxide) and tetrahydrofuran followed by separation and washing of the organic layer.

In one embodiment (R)-4-penten-2-yl p-toluenesulfonate is used to prepare (S)—N-methyl-4-penten-2-amine. In another embodiment (S)-4-penten-2-yl p-toluenesulfonate is used to prepare (R)-N-methyl-4-penten-2-amine.

The solvent is changed from N,N-dimethylformamide in the previous process to tetrahydrofuran. The work-up solvent is changed from ether to methyl tert-butyl ether. In the previous process the mixture needed to be dried, for example with sodium sulfate, and then distilled to reduce the amount of solvent. These steps are no longer necessary in the improved process.

The effect of these changes is that the overall reaction time for step 3 has been reduced from 48 h to 8 h.

The reaction temperature is raised to reflux.

Non-limiting examples of suitable ether solvents may be selected from the group comprising tetrahydrofuran, 2-methyltetrahydrofuran and 1,4-dioxane.

Step 4a of Scheme 1:

One aspect of the invention relates to process step 4a for the preparation of N-(tert-butoxycarbonyl)-N-methyl-4-penten-2-amine by addition of a mixture of di-tert-butyl dicarbonate in methyl tert-butyl ether to the reaction mixture obtained in step 3, followed by addition of N,N-dimethylethanediamine at full conversion of the (S)-N-methyl-4-penten-2-amine.

In a further embodiment N-(tert-butoxycarbonyl)-N-methyl-4-penten-2-amine is prepared by addition of a mixture of di-tert-butyl dicarbonate in methyl tert-butyl ether followed by addition of N,N-dimethylethanediamine at full conversion of the (S)-N-methyl-4-penten-2-amine and subsequent addition of water and hydrochloric acid until pH≤2 followed by separation and washing the organic phase, evaporating and distilling.

The reaction time is reduced from 16 h to 1 h by optimising the amount of di-tert-butyl dicarbonate and changing the charging order from adding di-tert-butyl dicarbonate to the solution to adding the solution to a solution of di-tert-butyl dicarbonate in methyl tert-butyl ether. N,N-dimethylethanediamine is added to the reaction to quench the excess of di-tert-butyl dicarbonate.

In one embodiment process step 4a is performed at a room temperature. Non-limiting examples of suitable solvents may be selected from the group comprising tetrahydrofuran, methyl tert-butyl ether and 2-methyltetrahydrofuran.

In one embodiment (S)-N-methyl-4-penten-2-amine is used to prepare (S)-N-(tert-butoxycarbonyl)-N-methyl-4-penten-2-amine. In another embodiment (R)-N-methyl-4-penten-2-amine is used to prepare (R)-N-(tert-butoxycarbonyl)-N-methyl-4-penten-2-amine.

The overall yield of process steps 1 to 4a is increased from 44% to about 50-55%.

The process shown in Scheme 1 may be used in reactors having a volume of 2.5 m³.

An alternative process for the preparation of the protected pentene-amine is by preparing N-methyl-4-penten-2-amine di-benzoyl-L-(−)-tartaric acid salt as shown in Scheme 2.

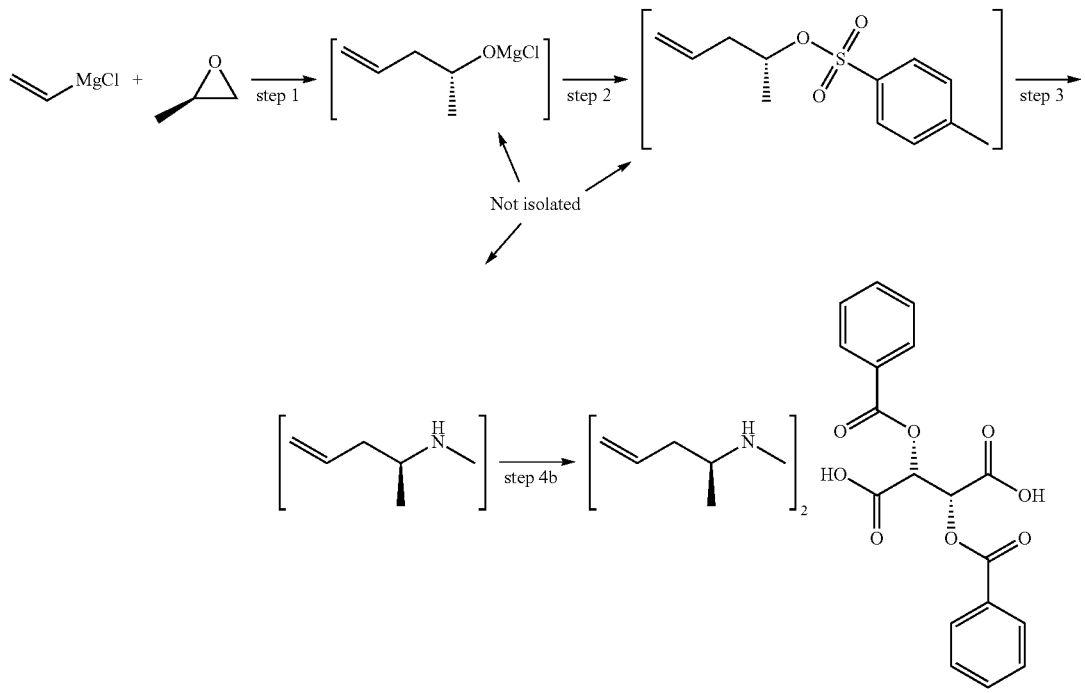

Scheme 2

Step 4b of Scheme 2:

In one aspect, N-methyl-4-penten-2-amine di-benzoyl-L-(−)-tartaric acid salt is prepared by addition of a solution of (L)-(−)-benzoyl-tartaric acid (0.5 mole-equivalent relative to N-methyl-4-penten-2-amine) to a solution of N-methyl-4-penten-2-amine in an organic solvent.

In an embodiment N-methyl-4-penten-2-amine di-benzoyl-L-(−)-tartaric acid salt is prepared by addition of a solution of (L)-(−)-benzoyl-tartaric acid (0.5 mole-equivalent) to a solution of N-methyl-4-penten-2-amine in an organic solvent, and washing using a 1:1 mixture of methyl tert-butyl ether and isooctane and drying under vacuum.

One embodiment relates to the compound N-methyl-4-penten-2-amine di-benzoyl-L-(−)-tartaric acid salt.

Acids that may be used to precipitate with N-methyl-4-penten-2-amine to yield a salt are, but not limited to, di-benzoyl-L-(−)-tartaric acid, oxalic acid, fumaric acid, succinic acid, citric acid, (+)-di-p-toluoyl-D-tartaric acid, (−)-di-p-toluoyl-L-tartaric acid, di-benzoyl-D-(+)-tartaric acid. In one embodiment the salt is a di-benzoyl-L-(−)-tartaric acid salt.

In a further embodiment process step 4b is performed at room temperature.

Non-limiting examples of suitable solvents may be selected from the group comprising methyl tert-butyl ether, diethyl ether and 2-methyltetrahydrofuran, 2-propanol, acetone, tetrahydrofuran, ethanol, isooctane and acetonitrile.

In another embodiment, the solvent is methyl tert-butyl ether.

In one embodiment, (S)-N-methyl-4-penten-2-amine is used to prepare (S)-N-methyl-4-penten-2-amine di-benzoyl-L-(−)-tartaric acid salt. In another embodiment, (R)-N-methyl-4-penten-2-amine is used to prepare (R)-N-methyl-4-penten-2-amine di-benzoyl-L-(−)-tartaric acid salt.

This process has two fewer steps than the previously described process and yields the intermediate N-methyl-4-penten-2-amine as a solid salt instead of an oil. The oil (N-methyl-4-penten-2-amine) otherwise needed to be amine-protected and distilled to accomplish purification, as described in the previous process. These cumbersome steps are no longer needed in the process described herein.

One embodiment of the invention relates to a process for the preparation of aryl substituted olefinic amines such as (2S)-(4E)-N-methyl-5-[3-(5-isopropoxypyridin)yl]-4-penten-2-amine and (2S)-(4E)-N-methyl-5-[3-(5-methoxypyridin)yl]-4-penten-2-amine comprising the steps shown in Scheme 3 and Scheme 4.

Scheme 3

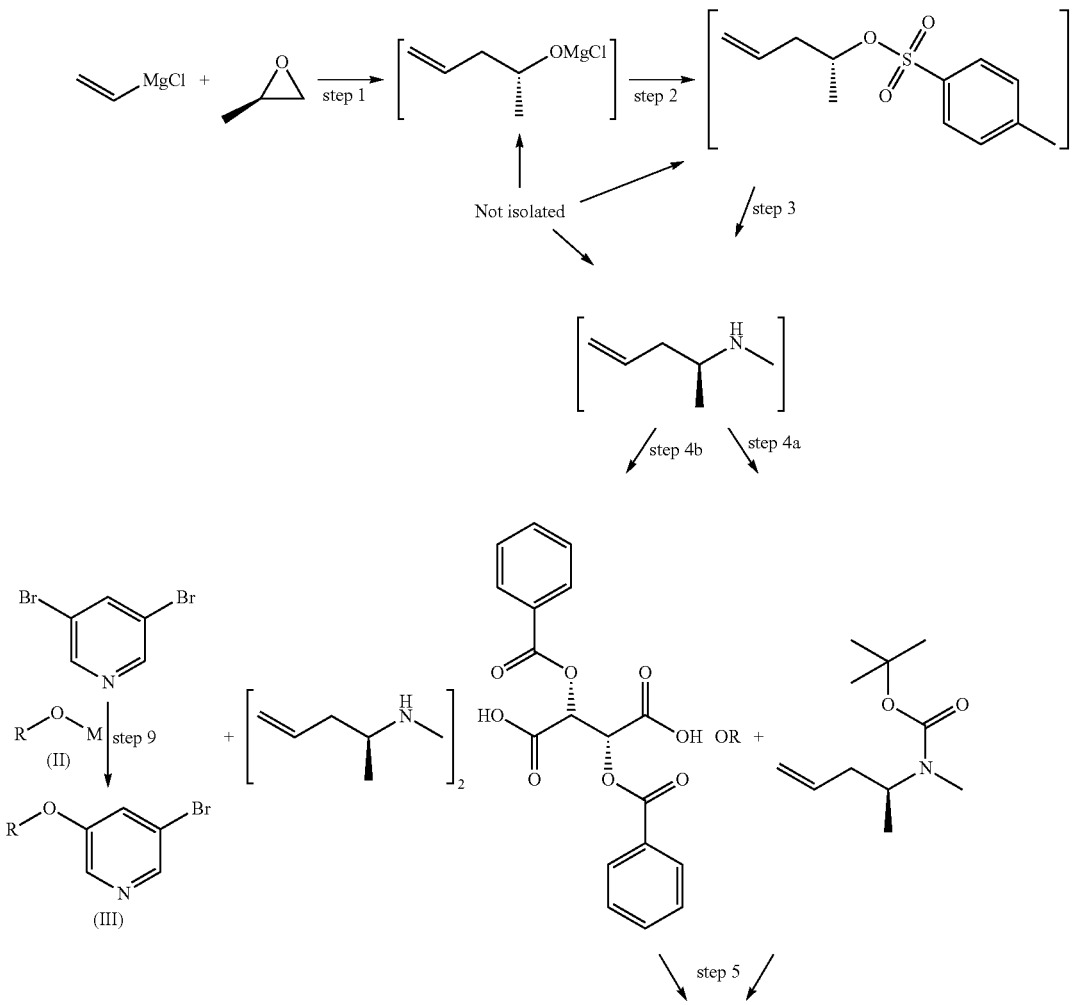

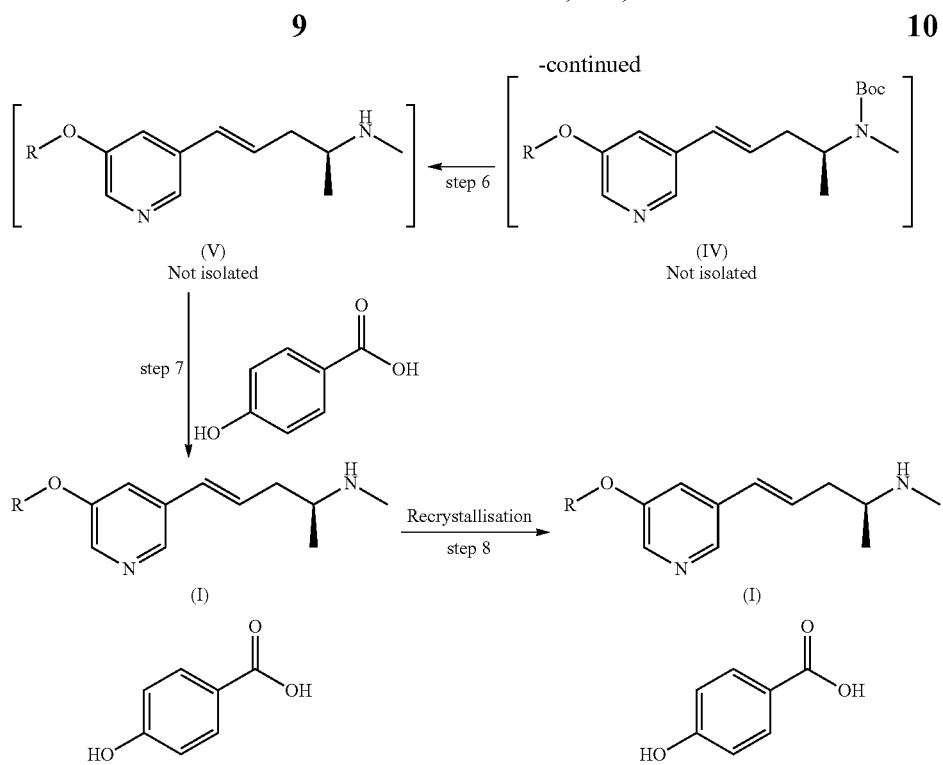

Step 1 of Scheme 3:

Preparation of 4-penten-2-ol by adding vinylmagnesium chloride to a mixture of copper(I) chloride and lithium chloride, followed by the addition of propylene oxide, in a suitable solvent, for example tetrahydrofuran;

Step 2 of Scheme 3:

Preparation of 4-penten-2-yl p-toluenesulfonate by adding the magnesium salt of 4-penten-2-ol to a solution of p-toluenesulfonyl chloride in tetrahydrofuran and subsequently transferring the mixture to a mixture of water and methyl tert-butyl ether followed by addition of an acid, such as hydrochloric acid, until acidic pH is obtained, separation and washing of the organic phase and distillation thereof;

Step 3 of Scheme 3:

Preparation of N-methyl-4-penten-2-amine by adding 4-penten-2-yl p-toluenesulfonate in tetrahydrofuran over time to a refluxing solution of 40% aqueous solution of methylamine 7.3 mole-equivalent relative to propylene oxide and tetrahydrofuran followed by separation and washing of the organic layer;

Step 4a of Scheme 3:

Preparation of N-(tert-butoxycarbonyl)-N-methyl-4-penten-2-amine by addition of a mixture of di-tert-butyl dicarbonate in methyl tert-butyl ether, followed by addition of N,N-dimethylethanediamine at full conversion of the (S)-N-methyl-4-penten-2-amine, and subsequent addition of water and hydrochloric acid until pH≤2 followed by separation and washing the organic phase, evaporating and distilling.

Step 4b of Scheme 3:

Preparation of N-methyl-4-penten-2-amine di-benzoyl-L-(−)-tartaric acid salt by addition of a solution of (L)-(−)-benzoyl-tartaric acid 0.5 mole-equivalent, to a solution of N-methyl-4-penten-2-amine in an organic solvent, and washing using a 1:1 mixture of methyl tert-butyl ether and isooctane and drying under vacuum.

The product of step 4a or 4b is used to prepare a final aryl substituted olefinic amine using the process as set out in steps 5, 6, 7 and 8 of Scheme 3 and Scheme 4.

Scheme 4

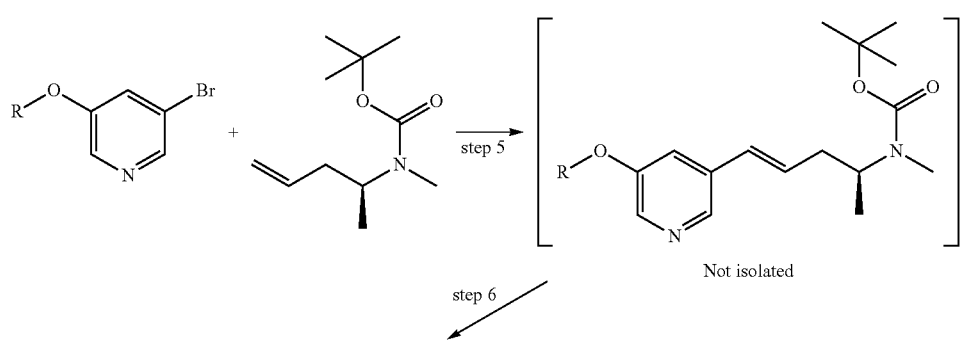

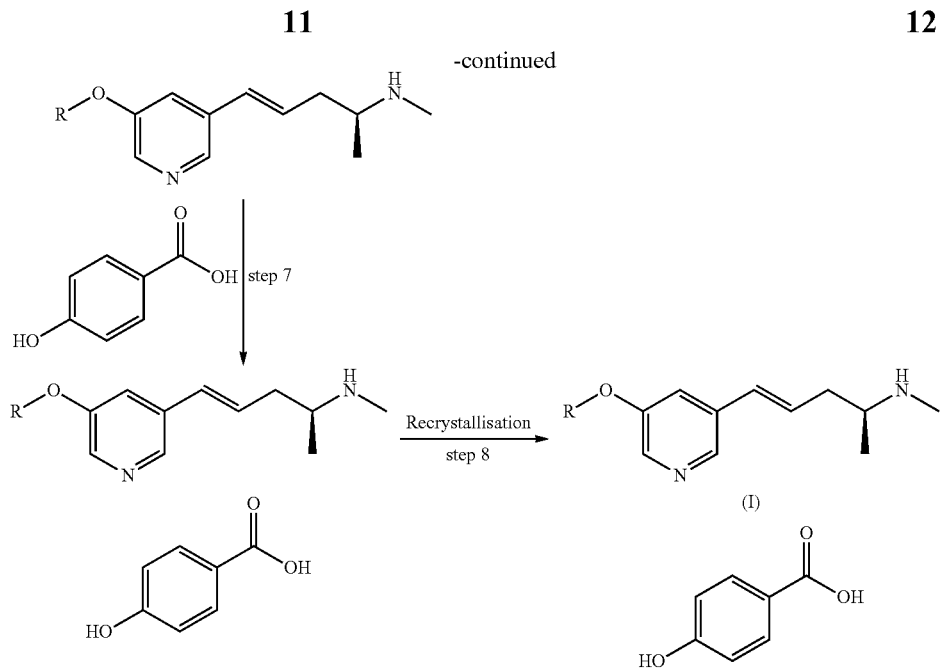

wherein in Scheme 4 R is a $C_{1-6}$alkyl such as methyl, ethyl, n-propyl, i-propyl, n-butyl, i-butyl, s-butyl, t-butyl, n-pentyl, i-pentyl, s-pentyl, n-hexyl or i-hexyl. In one embodiment, O—R is isopropoxy. In another embodiment, O—R is methoxy.

Steps 5 and 6 of Scheme 4:

One embodiment of the invention relates to process step 5 for the preparation of aryl substituted olefinic amines (I) such as (2S)-(4E)-N-methyl-5-[3-(5-isopropoxypyridin)yl]-4-penten-2-amine and (2S)-(4E)-N-methyl-5-[3-(5-methoxypyridin)yl]-4-penten-2-amine (the product) comprising the following steps;

a) mixing N-(tert-butoxycarbonyl)-N-methyl-4-penten-2-amine (1 mole-equivalent) and 5-bromo-3-alkoxypyridine (1.1 mole-equivalents) with a palladium source (0.01 mole-equivalents), a phosphine ligand (0.24 mole-equivalents) and a base (1.5 mole-equivalents) in a suitable organic solvent under an atmosphere of nitrogen;

b) adding water and heating the mixture to 90° C. for 15 to 25 h or until the appropriate level of conversion have been achieved;

c) cooling the mixture and adding water and an acid, such as hydrochloric acid, followed by stirring at 0-70° C. for 3 to 8 h;

d) separating the organic solvent and the acidic (product containing) aqueous phases followed by washing the aqueous phase with organic solvent;

e) adjustment of the pH in the aqueous phase by the addition of a base and extracting the product into the organic phase followed by separation of the organic phase; and optionally f) treating the organic phase with a metal scavenger or charcoal.

One embodiment of the invention relates to a process for the preparation of aryl substituted olefinic amines (I) such as (2S)-(4E)-N-methyl-5-[3-(5-isopropoxypyridin)yl]-4-penten-2-amine and (2S)-(4E)-N-methyl-5-[3-(5-methoxypyridin)yl]-4-penten-2-amine comprising the following steps;

Another non-limiting example of the process step 5 is a process for the preparation of N-methyl-5-[3-(5-isopropoxypyridin)yl]-4-penten-2-amine whereby N-(tert-butoxycarbonyl)-N-methyl-4-penten-2-amine (1 mole-equivalent) and 5-bromo-3-isopropoxypyridine (1.1 mole-equivalents) are mixed with palladium acetate (0.01 mole-equivalents), tri-o-tolylphosphine (0.25 mole-equivalents) and triethylamine (1.5 mole-equivalents) in toluene under an atmosphere of nitrogen. The mixture is inerted, a small amount of water is added and the mixture is heated to 90° C. and kept at this temperature for 20 h or until the appropriate level of conversion have been achieved as determined by gas chromatography analysis.

The mixture is cooled, and water and hydrochloric acid are added. The reaction mixture is stirred at 0-70° C. (e.g. 40° C.) for 5 h, whereafter the toluene and acidic (product containing) aqueous phases are separated. The aqueous phase is washed with toluene. The pH in the aqueous phase is adjusted to an alkaline pH by the addition of aqueous sodium hydroxide and the product is extracted into toluene. The phases are separated and the toluene phase is analysed for palladium. If the palladium content is below a predetermined limit the mixture is concentrated under reduced pressure to yield the product N-methyl-5-[3-(5-isopropoxypyridin)yl]-4-penten-2-amine.

If the palladium content is above a predetermined limit (not more than 20 ppm), the mixture is treated with a metal scavenger in order to reduce the palladium content and then concentrated under reduced pressure to yield the product N-methyl-5-[3-(5-isopropoxypyridin)yl]-4-penten-2-amine.

This new process for the preparation of N-methyl-5-[3-(5-isopropoxypyridin)yl]-4-penten-2-amine has several advantages over the previous method (WO2006/053082) and it is more suited for large scale manufacture.

In particular, the use of toluene, instead of N,N-dimethylformamide and dichloromethane, has the advantages of being cheaper, more environmentally friendly and giving a better process. Since toluene is not miscible with water, a two phase system is obtained after the addition of the water and hydrochloric acid. More than 99% of the palladium remains in the toluene phase, while the product is in the acidic aqueous phase and simple phase separation removes most of the palladium from the product.

During the subsequent evaporation of the solvent, the appropriate water content in the product is obtained directly due to the better azeotrope with toluene. With other solvents it may be necessary to do repeated solvent distillations to reach the low water content required for the next step.

Another advantage of the new process is the use of an excess of the 5-bromo-3-isopropoxypyridine in contrast to the previous method where the N-(tert-butoxycarbonyl)-N-methyl-4-penten-2-amine was used in excess.

In the previous method, the palladium precipitated as Pd(0) at the end of the reaction which could create problems regarding cleaning of the equipment. By using an excess of the 5-bromo-3-isopropoxypyridine the palladium catalyst remains as stable Pd(II) complexes at the end of the reaction and no precipitation of Pd(0) occurs.

The use of an excess of the 5-bromo-3-isopropoxypyridine gives a cheaper process compared to the previous process where the N-(tert-butoxycarbonyl)-N-methyl-4-penten-2-amine was used in excess, due to the lower cost of the 5-bromo-3-isopropoxypyridine.

Yet another advantage of the new process is the use of water as an additive. The addition of water increases the rate of the reaction and gives a more robust process by ensuring proper catalyst activation.

Another embodiment of the invention relates to a process for the preparation of N-methyl-5-[3-(5-isopropoxypyridin)yl]-4-penten-2-amine according to the process outlined above, but where the catalyst and toluene are reused in a series of consecutive batches. By this process the palladium containing toluene phase is kept in the reactor and put under an atmosphere of nitrogen and the cycle is repeated by the addition of N-(tert-butoxycarbonyl)-N-methyl-4-penten-2-amine (1 mole-equivalent) and 5-bromo-3-alkoxoxypyridine (1.1 mole-equivalents) and base (1.5 mole-equivalents) followed by heating etc.

This series of consecutive cycles may be repeated as many times as desired provided the proper quality of the product can be obtained.

The reuse of the palladium catalyst and toluene in a series of consecutive batches as described above has the advantage of significantly reducing both the cost and environmental impact of the process due to the much smaller amount of palladium and toluene that is required to produce a given amount of the product.

In one embodiment the solvent in step 5 is selected from an ether, ketone, aromatic hydrocarbon, ester, N,N-dialkylamide or alcohol. Non-limiting examples of solvents may be selected from the group comprising toluene, dioxane, methyl isobutyl ketone, n-butylacetate, iso-propylacetate, t-butylacetate, n-butanol, N,N-dimethylformamide, N,N-dimethylacetamide and 1-methyl-2-pyrrolidinone.

In one embodiment the solvent is toluene.

In another embodiment the base in step 5 is an amine. Non-limiting examples of amines may be selected from the group comprising triethylamine, diisopropylethylamine, diisopropylamine, dicyclohexylmethylamine, N-methylmorpholine and triethanolamine.

In one embodiment the base is triethylamine.

In a further embodiment the base in step 5 is an inorganic base. Non-limiting examples of inorganic bases may be potassium carbonate, sodium carbonate, sodium bicarbonate, sodium phosphate and sodium acetate.

The use of an inorganic base may have the advantage of providing a cheaper and more environmentally friendly process.

In one embodiment the base and solvent in step 5 are an arbitrary combination of any of the solvents and bases listed above.

The stucture of the phosphine ligand has a strong influence on the yield of the desired product. The ligand may be a phosphine, phosphite, phosphinite or phosphoramidite. In another embodiment the ligand is a mono or bis phosphine. Non-limiting examples of ligands may be selected from the group comprising triphenylphosphine, tri-o-tolylphosphine, tri-p-tolylphosphine, tri-p-methoxyphosphine, tri-p-fluorophenylphosphine, diphenyl-o-tolylphosphine, diphenyl-t-butylphosphine, diphenylcyclohexylphosphine, 2-(dicyclohexylphosphino)-2',4',6'-tri-i-propyl-1,1'-biphenyl, 2-(di-t-butylphosphino)biphenyl, 2-(dicyclohexylphosphino)biphenyl, tri-(2-furyl)phosphine, tricyclohexylphosphine, tri-t-butylphosphine, 1,2,3,4,5-pentaphenyl-1'-(di-t-butylphosphino)ferrocene, bis-(diphenylphosphino)methane, 1,2-bis-(diphenylphosphino)ethane, 1,3-bis-(diphenylphosphino)propane, 1,2-bis-(dicyclohexylphosphino)ethane, 1,1'-bis(diphenylphosphino)ferrocene, bis(diphenylphosphino)1,1'-binaphtyl, 4,5-bis(diphenylphosphino)9,9-dimethylxanthene, 1,2-bis(diphenylphosphino)benzene, triphenylphosphite, diisopropylphenylphosphinite, triisopropylphosphite, 2,8,9 trimethyl-2,5,8,9-tetraaza-1-phosphabicyklo[3.3.3]undekane, bis(dicyclohexylphosphino)methane, 2-dicyclohexylphosphino-2',6'-dimethoxy-1,1'-biphenyl, 2-(dicyclohexylphosphino)-2'-(N,N-dimethylamino)biphenyl, tris-(3,5-dimethyl-4-methoxyphenyl)phosphine, 1,1'-bis(di-t-butylphosphino)ferrocene, and tris-(4-methoxyphenyl)phosphine.

In one embodiment the phosphine ligand is tri-o-tolylphosphine.

In one embodiment the palladium source is a Pd(II) complex or a Pd(0) complex.

Non-limiting examples of Pd(II) complexes may be selected from the group comprising $Pd(OAc)_2$, $Cl_2Pd[P(o-tol)_3]_2$ and $Pd(TFA)_2$, $[PdCl_2(t-butyl)_2P(OH)]_2$ (CombiPhos POPd2), $\{PdCl[(t-butyl)_2P(O)][(t-butyl)_2P(OH)]\}_2$ (CombiPhos POPd1).

Non limiting examples of Pd(0) complexes may be selected from the group comprising $Pd(dba)_2$, $Pd_2(dba)_3$ and $Pd[P(o-tol)_3]_2$.

In one embodiment the palladium source is $Pd(OAc)_2$.

In embodiments in which the palladium source also contains phosphine ligands, such as $[PdCl_2(t-butyl)_2P(OH)]_2$, $\{PdCl[(t-butyl)_2P(O)][(t-butyl)_2P(OH)]\}_2$, $Cl_2Pd[P(o-tol)_3]_2$, and $Pd[P(o-tol)_3]_2$, an additional phosphine ligand is optional.

Non-limiting examples of the scavanger may be selected from the group comprising SiliCycle SiliaBond-Thiol™, Argonaut TMT, Polymer Labs TMT, Johnson Matthey Smopex® 234, Reaxa QuadraPure™ MPA, Reaxa QuadraPure™ IMDAZ.

Step 7 of Scheme 4:

In one embodiment N-methyl-5-[3-(5-isopropoxypyridin)yl]-4-penten-2-amine 4-hydroxybenzoate is prepared by addition of N-methyl-5-[3-(5-isopropoxypyridin)yl]-4-penten-2-amine and 4-hydroxybenzoic acid in an organic solvent.

In a further embodiment N-methyl-5-[3-(5-isopropoxypyridin)yl]-4-penten-2-amine 4-hydroxybenzoate is prepared by addition of N-methyl-5-[3-(5-isopropoxypyridin)yl]-4-penten-2-amine and 4-hydroxybenzoic acid in an organic solvent followed by isolating and washing the precipitate.

In another embodiment the organic solvent is acetone.

In one embodiment process step 7 is performed at a temperature of from 0° C. to reflux.

In one embodiment (2S)-(4E)-N-methyl-5-[3-(5-isopropoxypyridin)yl]-4-penten-2-amine is used to prepare (2S)-(4E)-N-methyl-5-[3-(5-isopropoxypyridin)yl]-4-penten-2-amine 4-hydroxybenzoate. In another embodiment (2R)-(4E)-N-methyl-5-[3-(5-isopropoxypyridin)yl]-4-penten-2-amine is used to prepare (2R)-(4E)-N-methyl-5-[3-(5-isopropoxypyridin)yl]-4-penten-2-amine 4-hydroxybenzoate.

Step 8 of Scheme 4:

Crystallisation is controlled by adding 4-hydroxybenzoic acid at 50° C. The clear solution may optionally be seeded to induce a desired form of crystals. The crystallisation process is changed from cooling to −15° C. to cooling the reaction to 0° C. and isolating the crystals.

One embodiment relates to a process for the preparation of (2S)-(4E)-N-methyl-5-[3-(5-isopropoxypyridin)yl]-4-penten-2-amine 4-hydroxybenzoate as shown in Scheme 3.

Another embodiment relates to the large scale manufacturing of aryl substituted olefinic amines (I) such as (2S)-(4E)-N-methyl-5-[3-(5-isopropoxypyridin)yl]-4-penten-2-amine and (2S)-(4E)-N-methyl-5-[3-(5-methoxypyridin)yl]-4-penten-2-amine as well as the hydroxybenzoate salt thereof.

A further embodiment relates to a process for the preparation of aryl substituted olefinic amines (I) such as (2S)-(4E)-N-methyl-5-[3-(5-isopropoxypyridin)yl]-4-penten-2-amine and (2S)-(4E)-N-methyl-5-[3-(5-methoxypyridin)yl]-4-penten-2-amine comprising process steps 1 to 7.

Yet a further embodiment relates to a process for the preparation of hydroxybenzoate salt of aryl substituted olefinic amines (I) such as (2S)-(4E)-N-methyl-5-[3-(5-isopropoxypyridin)yl]-4-penten-2-amine and (2S)-(4E)-N-methyl-5-[3-(5-methoxypyridin)yl]-4-penten-2-amine comprising process steps 1 to 8 of Scheme 3.

The process shown in Scheme 4 may be used in reactors having a volume of 4 m$^3$.

EXAMPLES

The invention will now be illustrated by the following non-limiting examples in which, generally: operations were carried out at room temperature, i.e. in the range 16 to 25° C.; evaporations were carried out by rotary evaporation in vacuo; chromatography (GC) was performed using an Ultra 2 column; yields, where present, are not necessarily the maximum attainable; in general, the structures of the end-products were confirmed by nuclear magnetic resonance (NMR) and/or mass spectral (MS) techniques; mass spectral data were obtained using Waters Micromass ZQ; NMR chemical shift values were measured on the delta scale [proton magnetic resonance spectra were determined using a Bruker Avance NMR spectrometer operating at a field strength of 400 MHz]; the following abbreviations have been used: s, singlet; d, doublet; t, triplet; m, multiplet; b, broad; dd, doublet doublet; dt, doublet triplet; intermediates were not necessarily fully purified but their structures and purity were assessed by GC and/or NMR analysis; melting points are uncorrected and were determined using a DSC, Perkin-Elmer DSC7 Differential Scanning calorimeter.

The following abbreviations are used herein:

BMAP (S)-N-(tert-butoxycarbonyl)-N-methyl-2-aminopent-4-ene, also named (S)-N-(tert-butoxycarbonyl)-N-methyl-4-penten-2-amine Boc$_2$O Di-tert-butyl dicarbonate
Cy$_2$NMe N,N-Dicyclohexylmethylamine
DMAC N,N-Dimethylacetamide
DMAEA N,N-Dimethylaminoethylamine
DMF N,N-dimethylformamide
equiv Mole-equivalents
Et$_3$N Triethylamine
GC Gas chromatography
MTBE Methyl tert-butyl ether
NMM N-Methylmorpholine
Pd(OAc)$_2$ Palladium acetate
i-Pr$_2$NEt N,N-Diisopropylethylamine
THF Tetrahydrofuran
TsCl p-Toluenesulfonyl chloride A) Steps 1 to 4a Step 4a (S)-N-(tert-butoxycarbonyl)-N-methyl-4-penten-2-amine A solution of (S)-N-methyl-4-penten-2-amine in MTBE was charged over time at ambient temperature to a solution of Boc$_2$O (113 kg, 518 mol) in MTBE (110 L). The mixture was stirred until more than 99.5% of (S)-N-methyl-4-penten-2-amine had been consumed (using GC). DMAEA (11.5 kg, 130 mol) was added over time at ambient temperature and the mixture was stirred until more than 99.5% of the Boc$_2$O had been consumed (using GC). Water (370 kg) was added, and hydrochloric acid was added until pH≤2. The phases were separated and the organic phase was washed with aqueous sodium chloride solution. The organic phase was evaporated to remove the solvent and further distilled under vacuum and heat to yield the title compound (125 kg).

Steps 1 and 2

The (S)-N-methyl-4-penten-2-amine used as a starting material was prepared as follows:

Copper(I) chloride (645 g, 6.52 mol) and lithium chloride (550 g, 12.9 mol) were dissolved in THF (140 L) and cooled to 0° C. Vinyl magnesium chloride (349 kg, 633 mol, 16.5% in THF) was added slowly, maintaining the temperature below 5° C. The mixture was cooled to −15° C. A cooled solution of R-propylene oxide (37.8 kg, 651 mol) in THF (900 L) was added slowly, maintaining the temperature below −15° C. The reaction mixture was stirred until more than 98.5% of R-propylene oxide had been consumed (using GC). The mixture was added slowly to a cooled solution of TsCl (127 kg, 664 mol) in THF (470 L). The mixture was heated to ambient temperature and stirred until more than 98% of the 4-penten-2(R)-ol had been consumed (using GC). The reaction mixture was transferred to a mixture of water (630 L) and MTBE (280 L). Hydrochloric acid was added until pH≤2.5. The phases were separated and the aqueous phase was washed with MTBE. The combined organic phases were washed with aqueous sodium chloride solution and the organic phase was distilled to remove MTBE, to yield (R)-4-penten-2-yl p-toluenesulfonate in a THF solution (190 L). THF (120 L) is then added to the solution.

$^1$H-NMR (CDCl3) δ 1.27 (d 3H), 2.33 (m 2H), 2.45 (s 3H), 4.65 (m 1H), 5.02 (t 1H), 5.05 (dt 1H), 5.61 (m 1H), 7.34 (d 2H), 7.80 (d 2H).

$^{13}$C-NMR (CDCl3) δ 20.3 CH3, 21.6 CH3, 40.7 CH2, 79.4 CH, 118.7 CH2, 127.7 CH, 129.8 CH, 132.2 CH, 134.4 C, 144.6 C.

MS m/z=240.1.

Step 3

A solution of (R)-4-penten-2-yl p-toluenesulfonate (310 L) in THF was added over time to a refluxing solution of 40% aqueous solution of methylamine (369 kg, 11.9 kmol) and THF (80 L). The reaction mixture was stirred until more than 99% of the (R)-4-penten-2-yl-p-toluenesulfonate had been consumed (using GC). The mixture was cooled, MTBE (370 L) was added and the phases were separated. The aqueous phase was washed two times with MTBE, and the combined organic phases were washed two times with aqueous sodium chloride (20%). The solution of (S)-N-methyl-4-penten-2-amine in MTBE was used in the next step.

$^1$H NMR (CD3CN) δ 0.97 (d 3H), 2.04 (m 1H), 2.15 (m 1H), 2.29 (s 3H), 2.53 (m 1H), 5.03 (t 1H), 5.04 (dd 1H), 5.80 (m 1H).

$^{13}$C-NMR (CD3CN) δ 19.8 CH3, 34.0 CH3, 41.7 CH2, 55.2 CH, 117.2 CH2, 137.2 CH.

B) Steps 1 to 4b
Step 4b

(S)-N-methyl-4-penten-2-amine di-benzoyl-L-(−)-tartaric acid salt

A solution of (L)-(−)-benzoyl-tartaric acid (0.20 kg, 0.57 mol) in MTBE (1.37 L) was added over 5 h to a solution of (S)-N-methyl-4-penten-2-amine (1.90 kg, 1.17 mol, 6.1%) in MTBE at ambient temperature. The mixture was stirred at ambient temperature for 6 h. The mixture was cooled to 0° C. over 6 h and stirred overnight. The resultant solid was isolated, washed using a 1:1 mixture of MTBE and isooctane and dried under vacuum at 25° C. to yield the title compound (0.29 kg).

$^1$H-NMR (CDCl3) δ 1.10 (d 6H), 2.14 (m 2H), 2.33 (s 6H), 2.37 (m 2H), 2.90 (m 2H), 4.95 (d 2H), 4.98 (s 2H), 5.57 (m 2H), 5.63 (s 2H), 7.52 (t 4H), 7.63 (t 2H), 8.01 (d 4H), 9.59 (b 4H).

$^{13}$C-NMR (CDCl3) δ 15.2 CH3, 29.2 CH3, 26.5 CH2, 52.9 CH, 75.6 CH, 118.3 CH2, 128.4 CH, 129.3 C, 130.9 C, 132.8 CH, 133.4 CH, 165.3 C, 170.2 C.

Mp=149.4-149.6° C.

Steps 1 and 2

The (S)-N-methyl-4-penten-2-amine used as a starting material was prepared as follows:

Copper(I) chloride (3.24 g, 32.4 mmol) and lithium chloride (2.75 g, 64.8 mmol) were dissolved in THF (0.64 L) and cooled to 0° C. Vinyl magnesium chloride (1.87 kg, 3.56 mol, 16.5% in THF) was added slowly, maintaining the temperature below 5° C. The mixture was cooled to −20° C. A cooled solution of R-propylene oxide (0.19 kg, 3.24 mol) in THF (0.41 L) was added slowly, maintaining the temperature below −10° C. The reaction mixture was stirred until more than 98.5% of the epoxide had been consumed (using GC). The mixture was added slowly to a cooled solution of TsCl (0.67 kg, 3.43 mol) in THF (1.72 L). The mixture was heated to ambient temperature and stirred until more than 98% of the 4-penten-2(R)-ol had been consumed (using GC). The reaction mixture was transferred to a cool mixture of water (2.28 L) and MTBE (1.54 L). Hydrochloric acid (65.5 g) was added until a slightly acidic pH was obtained. The phases were separated and the aqueous phase was washed with MTBE. The combined organic phases were washed with aqueous sodium chloride solution and the organic phase was distilled to remove MTBE, to yield (R)-4-penten-2-yl p-toluenesulfonate in a THF solution.

$^1$H-NMR (CDCl3) δ 1.27 (d 3H), 2.33 (m 2H), 2.45 (s 3H), 4.65 (m 1H), 5.02 (t 1H), 5.05 (dt 1H), 5.61 (m 1H), 7.34 (d 2H), 7.80 (d 2H).

$^{13}$C-NMR (CDCl3) δ 20.3 CH3, 21.6 CH3, 40.7 CH2, 79.4 CH, 118.7 CH2, 127.7 CH, 129.8 CH, 132.2 CH, 134.4 C, 144.6 C.

MS m/z=240.1.

Step 3

A solution of (R)-4-penten-2-yl p-toluenesulfonate (1.80 kg) in THF was added over time to a refluxing solution of 40% aqueous solution of methylamine (24.3 mol, 1.89 kg). The reaction mixture was stirred until more than 99% of the (R)-4-penten-2-yl p-toluenesulfonate had been consumed (using GC). The mixture was cooled and pH was adjusted to 14 using aqueous sodium hydroxide. MTBE was added and the phases were separated. The aqueous phase was washed two times with MTBE and the combined organic phases were washed two times with aqueous sodium chloride. The organic phase was dried with sodium sulphate to yield 3.47 kg of (S)-N-methyl-4-penten-2-amine.

$^1$H NMR (CD3CN) δ 0.97 (d 3H), 2.04 (m 1H), 2.15 (m 1H), 2.29 (s 3H), 2.53 (m 1H), 5.03 (t 1H), 5.04 (dd 1H), 5.80 (m 1H).

$^{13}$C-NMR (CD3CN) δ 19.8 CH3, 34.0 CH3, 41.7 CH2, 55.2 CH, 117.2 CH2, 137.2 CH.

C) Steps 5 to 8
Steps 5 and 6

(2S)-(4E)-N-methyl-5-[3-(5-isopropoxypyridin)yl]-4-penten-2-amine

Toluene (430 kg) and triethylamine (95 kg, 939 mol) were added to a reactor at ambient temperature. To the stirred solution, Pd(OAc)$_2$ (1.41 kg, 6.28 mol) and tri-(o-tolyl)phosphine (4.77 kg, 15.7 mol) were added. Several inertations were performed and the mixture was stirred until a clear solution was obtained. BMAP (125 kg, 627 mol) and 3-bromo-5-isopropoxypyridine (149 kg, 690 mol) were added, followed by repeated inertations. Water (1.1 kg, 61.1 mol) was added and the inertations were repeated. The mixture was heated to 90° C. and stirred until more than 97% of the BMAP had been consumed (using GC). Water (380 kg) and hydrochloric acid (185 kg, 1882 mol) were added over time to maintain the temperature under 40° C. The mixture was heated to 40° C. and stirred until more than 99.5% of the protected product had been consumed (using gas chromatography). The phases were separated and the aqueous phase was washed with toluene (220 kg). Toluene (330 kg) and aqueous sodium hydroxide (98 kg) were added over time to retain the temperature under 40° C. The mixture was stirred for 20 min and the phases were separated. The organic phase was distilled to yield the title compound (111 kg, 0.474 kmol).

$^1$H NMR (400 MHz CDCl$_3$) δ 0.95 (d, 3H, J=6.4 Hz), 1.20 (d, 6H, J=6.0 Hz), 2.08-2.25 (m, 2H), 2.28 (s, 3H), 2.55 (m, 1H), 4.45 (sept, 1H, 6.0 Hz), 6.06-6.17 (dt, 1H, J=7.5 Hz, 16.0 Hz), 6.25 (d, 1H, 16.0 Hz), 7.02 (m, 1H), 7.96-7.99 (m, 1H), 8.00-8.03 (m, 1H)

$^{13}$C NMR (100 MHz CDCl$_3$) δ 19.7, 21.5, 33.9, 40.3, 54.4, 70.3, 118.7, 128.7, 129.9, 133.5, 137.5, 140.2, 153.8

Step 5 Using Different Solvents and Bases
1. n-Butylacetate as Solvent, Triethylamine as Base To a 50 mL reaction vessel were added, under an atmosphere of nitrogen, Pd(OAc)$_2$ (33.5 mg, 149 µmol), tris(2-methylphenyl)phosphine (104 mg, 343 µmol), 3-bromo-5-isopropoxypyridine (3.70 g, 16.4 mmol), N-Boc-N-methyl-4-pentene-2-amine (3.00 g, 14.9 mmol), triethylamine (2.3 g, 22.4 mmol) and n-butylacetate 9 mL. The mixture was then stirred at 90° C. for 18 h. The mixture was cooled to 40° C. and water (9 mL) followed by hydrochloric acid 37% (aq) (3.7 mL, 44.7 mmol) was added. The mixture was stirred at 40° C. for 4 h. The phases were separated and the aqueous layer containing the product was washed with toluene (6 mL). Toluene (9 mL) and sodium hydroxide 50% (aq) was added and the mixture was stirred for 15 min. The phases were separated and the toluene layer was evaporated to yield the product, 2.92 g, with a GC purity of 74%. $^1$H NMR spectroscopic data were in accordance with the above example (in Step 5 and 6), (2S)-(4E)-N-methyl-5-[3-(5-isopropoxypyridin)yl]-4-penten-2-amine.

2. Methyl Isobutyl Ketone as Solvent, Triethylamine as Base

To a 50 mL reaction vessel were added, under an atmosphere of nitrogen, Pd(OAc)$_2$ (33.5 mg, 149 µmol), tris(2-methylphenyl)phosphine (104 mg, 343 µmol), 3-bromo-5-isopropoxypyridine (3.70 g, 16.4 mmol), N-Boc-N-methyl-4-pentene-2-amine (3.00 g, 14.9 mmol), triethylamine (2.3 g, 22.4 mmol) and methyl isobutyl ketone 9 mL. The mixture was then stirred at 90° C. for 18 h. The mixture was cooled to 40° C. and water (9 mL) followed by hydrochloric acid 37% (aq) (3.7 mL, 44.7 mmol) was added. The mixture was stirred at 40° C. for 4 h. The phases were separated and the aqueous layer containing the product was washed with toluene (6 mL). Toluene (9 mL) and sodium hydroxide 50% (aq) was added and the mixture was stirred for 15 min. The phases were separated and the toluene layer was evaporated to yield the product, 2.89 g, with a GC purity of 74%. $^1$H NMR spectroscopic data were in accordance with example in Step 5 and 6, (2S)-(4E)-N-methyl-5-[3-(5-isopropoxypyridin)yl]-4-penten-2-amine.

3. Isopropyl Acetate as Solvent, Triethylamine as Base

To a 50 mL reaction vessel were added, under an atmosphere of nitrogen, Pd(OAc)$_2$ (33.5 mg, 149 µmol), tris(2-methylphenyl)phosphine (104 mg, 343 µmol), 3-bromo-5-isopropoxypyridine (3.70 g, 16.4 mmol), N-Boc-N-methyl-4-pentene-2-amine (3.00 g, 14.9 mmol), triethylamine (2.3 g, 22.4 mmol) and isopropyl acetate 9 mL. The mixture was then stirred at 90° C. for 18 h. The mixture was cooled to 40° C. and water (9 mL) followed by hydrochloric acid 37% (aq) (3.7 mL, 44.7 mmol) was added. The mixture was stirred at 40° C. for 4 h. The phases were separated and the aqueous layer containing the product was washed with toluene (6 mL). Toluene (9 mL) and sodium hydroxide 50% (aq) was added and the mixture was stirred for 15 min. The phases were separated and the toluene layer was evaporated to yield the product, 2.95 g, with a GC purity of 75%. $^1$H NMR spectroscopic data were in accordance with example in Step 5 and 6, (2S)-(4E)-N-methyl-5-[3-(5-isopropoxypyridin)yl]-4-penten-2-amine.

4. Toluene as Solvent, Triethanolamine as Base

To a 50 mL reaction vessel were added, under an atmosphere of nitrogen, Pd(OAc)$_2$ (33.5 mg, 149 µmol), tris(2-methylphenyl)phosphine (104 mg, 343 µmol), 3-bromo-5-isopropoxypyridine (3.70 g, 16.4 mmol), N-Boc-N-methyl-4-pentene-2-amine (3.00 g, 14.9 mmol), triethanolamine (3.3 g, 22.4 mmol) and toluene 9 mL. The mixture was then stirred at 90° C. for 18 h. The mixture was cooled to 40° C. and water (9 mL) followed by hydrochloric acid 37% (aq) (3.7 mL, 44.7 mmol) was added. The mixture was stirred at 40° C. for 4 h. The phases were separated and the aqueous layer containing the product was washed with toluene (6 mL). Toluene (9 mL) and sodium hydroxide 50% (aq) was added and the mixture was stirred for 15 min. The phases were separated and the toluene layer was evaporated to yield the product, 2.93 g, with a GC purity of 72%. $^1$H NMR spectroscopic data were in accordance with example in Step 5 and 6, (2S)-(4E)-N-methyl-5-[3-(5-isopropoxypyridin)yl]-4-penten-2-amine.

5. n-Butyl Acetate as Solvent, Triethanolamine as Base

To a 50 mL reaction vessel were added, under an atmosphere of nitrogen, Pd(OAc)$_2$ (33.5 mg, 149 µmol), tris(2-methylphenyl)phosphine (104 mg, 343 µmol), 3-bromo-5-isopropoxypyridine (3.70 g, 16.4 mmol), N-Boc-N-methyl-4-pentene-2-amine (3.00 g, 14.9 mmol), triethanolamine (3.3 g, 22.4 mmol) and n-butyl acetate 9 mL. The mixture was then stirred at 90° C. for 18 h. The mixture was cooled to 40° C. and water (9 mL) followed by hydrochloric acid 37% (aq) (3.7 mL, 44.7 mmol) was added. The mixture was stirred at 40° C. for 4 h. The phases were separated and the aqueous layer containing the product was washed with toluene (6 mL). Toluene (9 mL) and sodium hydroxide 50% (aq) was added and the mixture was stirred for 15 min. The phases were separated and the toluene layer was evaporated to yield the product, 2.91 g, with a GC purity of 70%. $^1$H NMR spectroscopic data were in accordance with example in Step 5 and 6, (2S)-(4E)-N-methyl-5-[3-(5-isopropoxypyridin)yl]-4-penten-2-amine 6. Methyl Isobutyl Ketone as Solvent, Triethanolamine as Base To a 50 mL reaction vessel were added, under an atmosphere of nitrogen, Pd(OAc)$_2$ (33.5 mg, 149 µmol), tris(2-methylphenyl)phosphine (104 mg, 343 µmol), 3-bromo-5-isopropoxypyridine (3.70 g, 16.4 mmol), N-Boc-N-methyl-4-pentene-2-amine (3.00 g, 14.9 mmol), triethanolamine (3.3 g, 22.4 mmol) and methyl isobutyl ketone 9 mL. The mixture was then stirred at 90° C. for 18 h. The mixture was cooled to 40° C. and water (9 mL) followed by hydrochloric acid 37% (aq) (3.7 mL, 44.7 mmol) was added. The mixture was stirred at 40° C. for 4 h. The phases were separated and the aqueous layer containing the product was washed with toluene (6 mL). Toluene (9 mL) and sodium hydroxide 50% (aq) was added and the mixture was stirred for 15 min. The phases were separated and the toluene layer was evaporated to yield the product, 2.90 g, with a GC purity of 70%. $^1$H NMR spectroscopic data were in accordance with example in Step 5 and 6, (2S)-(4E)-N-methyl-5-[3-(5-isopropoxypyridin)yl]-4-penten-2-amine.

7. Toluene as Solvent, Aqueous Sodium Acetate as Base

To a 50 mL reaction vessel were added, under an atmosphere of nitrogen, Pd(OAc)$_2$ (33.5 mg, 149 µmol), tris(2-methylphenyl)phosphine (104 mg, 343 µmol), 3-bromo-5-isopropoxypyridine (3.70 g, 16.4 mmol), N-Boc-N-methyl-4-pentene-2-amine (3.00 g, 14.9 mmol), aqueous sodium acetate 23% (9.3 mL, 29.8 mmol) and toluene 9 mL. The mixture was then stirred at 90° C. for 18 h. The mixture was cooled to 40° C. and water (9 mL) followed by hydrochloric acid 37% (aq) (3.7 mL, 44.7 mmol) was added. The mixture was stirred at 40° C. for 4 h. The phases were separated and the aqueous layer containing the product was washed with toluene (6 mL). Toluene (9 mL) and sodium hydroxide 50% (aq) was added and the mixture was stirred for 15 min. The phases were separated and the toluene layer was evaporated to yield the product, 3.17 g, with a GC purity of 65%. $^1$H NMR spectroscopic data were in accordance with example in Step 5 and 6, (2S)-(4E)-N-methyl-5-[3-(5-isopropoxypyridin)yl]-4-penten-2-amine.

8. Toluene as Solvent, Aqueous Potassium Carbonate as Base

To a 50 mL reaction vessel were added, under an atmosphere of nitrogen, Pd(OAc)$_2$ (33.5 mg, 149 µmol), tris(2-methylphenyl)phosphine (104 mg, 343 µmol), 3-bromo-5-isopropoxypyridine (3.70 g, 16.4 mmol), N-Boc-N-methyl-4-pentene-2-amine (3.00 g, 14.9 mmol), aqueous potassium carbonate 26% (9.0 mL, 22.4 mmol) and toluene 9 mL. The mixture was then stirred at 90° C. for 18 h. The mixture was cooled to 40° C., and water (9 mL) followed by hydrochloric acid 37% (aq) (3.7 mL, 44.7 mmol) was added. The mixture was stirred at 40° C. for 4 h. The phases were separated and the aqueous layer containing the product was washed with toluene (6 mL). Toluene (9 mL) and sodium hydroxide 50% (aq) was added and the mixture was stirred for 15 min. The phases were separated and the toluene layer was evaporated to yield the product, 2.87 g, with a GC purity of 64%. $^1$H NMR spectroscopic data were in accordance with example in Step 5 and 6, (2S)-(4E)-N-methyl-5-[3-(5-isopropoxypyridin)yl]-4-penten-2-amine.

Step 5. Heck Reaction with Recycling of the Catalyst
Cycle 1

Palladium acetate (111 mg, 496 μmol), tri-o-tolylphosphine (378 mg, 1.24 mmol), toluene (30 mL), triethylamine (10.3 mL, 75 mmol), 3-bromo-5-isopropoxypyridine (12.9 g, 54.6 mmol) and N-Boc-N-methyl-4-pentene-2-amine (10.0 g, 49.7 mmol) were added to a 250 mL Schlenk flask with a magnetic stir bar. The flask was evacuated and refilled with nitrogen gas twice followed by one minute of nitrogen purging and then heated to 90° C. The mixture was stirred at this temperature for 22 h at which point GC analysis indicated 98% conversion of the N-Boc-N-methyl-4-pentene-2-amine and concurrent formation of the coupling product N-boc-N-methyl-5-(5-isopropoxy-3-pyridinyl)-4-penten-2-amine.

The mixture was cooled to room temperature. Water (30 mL) and 37% aqueous hydrochloric acid (12 mL) was charged and the mixture was stirred at 40° C. for 5 h. The mixture was transferred to a separatory funnel and the phases were separated.

Cycle 2

The catalyst containing toluene layer was transferred back to the Schlenk flask and triethylamine (10.3 mL, 75 mmol), 3-bromo-5-isopropoxypyridine (12.9 g, 54.6 mmol) and N-Boc-N-methyl-4-pentene-2-amine (10.0 g, 49.7 mmol) were added. The flask was evacuated and refilled with nitrogen gas twice followed by one minute of nitrogen purging and then heated to 90° C. The mixture was stirred at this temperature for 22 h at which point GC analysis indicated 98% conversion of the N-Boc-N-methyl-4-pentene-2-amine and concurrent formation of the coupling product N-boc-N-methyl-5-(5-isopropoxy-3-pyridinyl)-4-penten-2-amine. The mixture was then cooled to room temperature. Water (30 mL) and 37% aqueous hydrochloric acid (12 mL) was charged and the mixture was stirred at 40° C. for 5 h. The mixture was transferred to a separatory funnel and the phases were separated.

Cycle 3

The catalyst containing toluene layer was transferred back to the Schlenk flask and triethylamine (10.3 mL, 75 mmol), 3-bromo-5-isopropoxypyridine (12.9 g, 54.6 mmol) and N-Boc-N-methyl-4-pentene-2-amine (10.0 g, 49.7 mmol) were added. The flask was evacuated and refilled with nitrogen gas twice followed by one minute of nitrogen purging and then heated to 90° C. The mixture was stirred at this temperature for 22 h at which point GC analysis indicated 98% conversion of the N-Boc-N-methyl-4-pentene-2-amine and concurrent formation of the coupling product N-boc-N-methyl-5-(5-isopropoxy-3-pyridinyl)-4-penten-2-amine. The mixture was then cooled to room temperature. Water (30 mL) and 37% aqueous hydrochloric acid (12 mL) was charged and the mixture was stirred at 40° C. for 5 h. The mixture was transferred to a separatory funnel and the phases were separated.

The sequence was repeated until 9 cycles had been completed with no reduction in product yield or reaction rate as determined by GC.

Step 5. Screen of Phosphine Ligands

To each of 34 4-mL vials were added ligand (38 μmol for monophosphines, 20 μmol for bisphosphines) and Pd(OAc)$_2$ (4.2 mg, 18.7 μmol) according to Table 1. Then 1.5 mL of a stock solution in DMAC containing 3-bromo-5-isopropoxypyridine (200 mg, 0.926 mmol), N-Boc-N-methyl-4-pentene-2-amine (221 mg, 1.1 mmol) naphthalene (309 mg) and diisopropylethylamine (179 mg, 1.4 mmol) was added and the vials were sealed and heated to 90° C. The reactions were monitored until full conversion of the 3-bromo-5-isopropoxypyridine was achieved and the mixtures were analysed by GC and the desired product/naphthalene peak areas were determined. The results are presented in table 1.

TABLE 1

Yields obtained with alternative ligands in step 5.

| Experiment | Ligand | % Yield of boc protected N-methyl-5-(5-isopropoxy-3-pyridinyl)-4-penten-2-amine (determined by GC) |
|---|---|---|
| 1 | Triphenylphosphine (PPh$_3$) | 51 |
| 2 | Tri-o-tolylphosphine (P(o-tol)$_3$) | 80 |
| 3 | Tri-p-tolylphosphine (P(p-tol)$_3$) | 40 |
| 4 | Tri-p-methoxyphosphine (P(p-OMePh)$_3$) | 49 |
| 5 | Tri-p-fluorophenylphosphine (P(p-FPh)$_3$) | 46 |
| 6 | Diphenyl-o-tolylphosphine (P(o-tol)Ph$_2$) | 50 |
| 7 | Diphenyl-t-butylphosphine (P(t-Bu)Ph$_2$) | 59 |
| 8 | Diphenylcyclohexylphosphine (PCyPh$_2$) | 48 |
| 9 | 2-(dicyclohexylphosphino)-2',4',6'-tri-i-propyl-1,1'-biphenyl (X-Phos) | 78 |
| 10 | 2-(di-t-butylphosphino)biphenyl ((t-Bu)$_2$Pbiphen) | 70 |
| 11 | 2-(dicyclohexylphosphino)biphenyl (Cy$_2$Pbiphen) | 80 |
| 12 | Tri-(2-furyl)phosphine (P(fur)$_3$) | 53 |
| 13 | Tricyclohexylphosphine (P(Cy)$_3$) | 67 |
| 14 | Tri-t-butylphosphine (P(t-Bu)$_3$) | 31 |
| 15 | 1,2,3,4,5-pentaphenyl-1'-(di-t-butylphosphino)ferrocene (Q-Phos) | 70 |
| 16 | Bis-(diphenylphosphino)methane (dppm) | 62 |
| 17 | 1,2-Bis-(diphenylphosphino)ethane (dppe) | 54 |
| 18 | 1,3-Bis-(diphenylphosphino)propane (dppp) | 59 |

TABLE 1-continued

Yields obtained with alternative ligands in step 5.

| Experiment | Ligand | % Yield of boc protected N-methyl-5-(5-isopropoxy-3-pyridinyl)-4-penten-2-amine (determined by GC) |
|---|---|---|
| 19 | 1,2-Bis-(dicyclohexylphosphino)ethane (dcpe) | 62 |
| 20 | R-(−)-1-[(S)-2-(dicyclohexylphosphino)ferrocenyl]ethyl-di-t-butylphosphine (Josiphos) | No reaction |
| 21 | 1,1'-bis(diphenylphosphino)ferrocene (dppf) | 71 |
| 22 | Bis(diphenylphosphino)1,1'-binaphthyl (binap) | 72 |
| 23 | 4,5-bis(diphenylphosphino)9,9-dimethylxanthene (xantphos) | 77 |
| 24 | 1,2-bis(diphenylphosphino)benzene (1,2-PPh2benz) | No reaction |
| 25 | Triphenylphosphite (P—OPh$_3$) | 61 |
| 26 | Diisopropylphenylphosphinite (iPr$_2$P—OPh) | 60 |
| 27 | Triisopropylphosphite (P(—OiPr)$_3$) | 60 |
| 28 | 2,8,9 trimethyl-2,5,8,9-tetraaza-1-phosphabicyklo[3.3.3]undekane (verkade base) | 48 |
| 29 | Bis(dicyclohexylphosphino)methane (dcpm) | 54 |
| 30 | 2-dicyclohexylphosphino-2',6'-dimethoxy-1,1'-biphenyl (s-phos) | 72 |
| 31 | 2-(dicyclohexylphosphino)-2'-(N,N-dimethylamino)biphenyl (Davephos) | 71 |
| 32 | Tris-(3,5-dimethyl-4-methoxyphenyl)phosphine (3,5-Me-4-Ome—Ph$_3$P) | 56 |
| 33 | 1,1'-bis(di-t-butylphosphino)ferrocene (bdtbf) | 59 |
| 34 | Tris-(4-methoxyphenyl)phosphine (P(4-OMePh)$_3$) | 71 |

Step 5. Screen of Amine Bases

To each of 20 4-mL vials were added ligand (38 μmol for monophosphines, 20 μmol for bisphosphines), Pd(OAc)$_2$ (4.2 mg, 18.7 μmol) and amine (1.4 mmol) according to Table 2. Then 1.2 mL of a stock solution in toluene containing: 3-bromo-5-isopropoxypyridine (200 mg, 0.926 mmol), N-Boc-N-methyl-4-pentene-2-amine (221 mg, 1.1 mmol) and naphthalene (119 mg) was added and the vials were sealed and heated to 90° C. The reactions were monitored until full conversion of the 3-bromo-5-isopropoxypyridine was achieved and the mixtures were analysed by gas chromatography and the desired product/naphthalene peak areas were determined. The results are presented in table 2.

TABLE 2

Yields obtained with alternative amines in step 5.

| Experiment | Amine | Ligand | GC product area/naphthalene area |
|---|---|---|---|
| 1 | Et$_3$N | P(o-tol)$_3$ | 1.23 |
| 2 | Et$_3$N | Dppf | 1.32 |
| 3 | Et$_3$N | Binap | 1.19 |
| 4 | Et$_3$N | xantphos | 1.1 |
| 5 | i-Pr$_2$NEt | P(o-tol)$_3$ | 1.21 |
| 6 | i-Pr$_2$NEt | Dppf | 1.05 |
| 7 | i-Pr$_2$NEt | Binap | 1.03 |
| 8 | i-Pr$_2$NEt | xantphos | 1.1 |
| 9 | i-Pr$_2$NEt | P(o-tol)$_3$ | 1.26 |
| 10 | i-Pr$_2$NEt | Dppf | 1.2 |
| 11 | i-Pr$_2$NEt | Binap | 1.22 |
| 12 | i-Pr$_2$NEt | xantphos | 1.13 |
| 13 | Cy$_2$NMe | P(o-tol)$_3$ | 1.27 |
| 14 | Cy$_2$NMe | Dppf | 1.11 |
| 15 | Cy$_2$NMe | Binap | 1.17 |
| 16 | Cy$_2$NMe | xantphos | 1.12 |
| 17 | NMM | P(o-tol)$_3$ | 1.21 |
| 18 | NMM | Dppf | 1.13 |
| 19 | NMM | Binap | 1.19 |
| 20 | NMM | xantphos | 1.16 |

Step 5. Screen of Palladium Sources

To each of five 4-mL vials was added catalyst (25 μmol) according to Table 3. Then 1.2 mL of a stock solution in toluene containing: 3-bromo-5-isopropoxypyridine (200 mg, 0.926 mmol), N-Boc-N-methyl-4-pentene-2-amine (221 mg, 1.1 mmol) and naphthalene (119 mg) was added and the vials were sealed and heated to 90° C. for 7 h and then analysed by GC. The results are presented in table 3.

TABLE 3

Yields obtained with alternative catalysts in step 5.

| Experiment | Catalyst | GC conversion after 7 h |
|---|---|---|
| 1 | Pd[P(o-tol)$_3$]$_2$ | 88% |
| 2 | Pd(OAc)$_2$ + P(o-tol)$_3$ | 73% |

TABLE 3-continued

Yields obtained with alternative catalysts in step 5.

| Experiment | Catalyst | GC conversion after 7 h |
|---|---|---|
| 3 | Pd(TFA)$_2$ + P(o-tol)$_3$ | 77% |
| 4 | Cl$_2$Pd[P(o-tol)$_3$]$_2$ | 46% |
| 5 | Pd(dba)$_2$ | 84% |

Steps 7 and 8

(2S)-(4E)-N-methyl-5-[3-(5-isopropoxypyridin)yl]-4-penten-2-amine 4-hydroxybenzoate A mixture of (2S)-(4E)-N-methyl-5-[3-(5-isopropoxypyridin)yl]-4-penten-2-amine (111 kg, 0.474 kmol) and acetone (1200 kg) were heated to 51° C. 4-Hydroxybenzoic acid (81 kg, 0.586 kmol) was added and the clear solution was cooled to 45° C. The solution was optionally seeded (0.45 kg, 1.21 mol) and stirred for 0.5 h to let the crystallisation start. The slurry was cooled to 0° C. over time and the crystals were isolated. The cake was washed with acetone (840 kg). Acetone (930 kg) was added to the wet crystals and the slurry was heated to 55° C. Water (16 kg) was added until a clear solution was obtained. The solution was clear filtered and cooled to 45° C., optionally seeded (0.90 kg, 2.42 mol) and stirred for 0.5 h to let the crystallisation start. The slurry was cooled to 0° C. over time and the crystals were isolated. The cake was washed with acetone (840 kg) and dried at 70° C. under vacuum to yield the title compound (141 kg).

$^1$H NMR (400 MHz DMSO-d$_6$) δ 1.10 (d, 3H, J=6.5 HZ), 1.26 (d, 6H, J=6.0 Hz), 2.22-2.35 (m, 1H), 2.39 (s, 3H), 2.43-2.48 (m, 1H), 2.88 (m, 1H), 4.71 (sept, 1H, J=6.0 Hz), 6.44-6.48 (m, 2H), 6.72-6.78 (m, 2H), 7.42 (m, 1H), 7.72-7.78 (m, 2H), 8.08 (m, 1H), 8.14 (m, 1H)

$^{13}$C NMR (100 MHz DMSO-d$_6$) δ 17.9, 31.7, 38.1, 53.8, 69.8, 114.6, 118.1, 125.1, 128.4, 129.7, 131.1, 133.5, 137.6, 139.9, 153.7, 160.5, 168.7

Examples of the Use of CombiPhos Catalyst in Step 5

In a series of experiments, the use of either of two CombiPhos catalyst (POPd1 and POPd2) in step 5 provided coupling product, (2S)-(4E)-N-methyl-5-[3-(5-isopropoxypyridin)yl]-4-penten-2-amine, in yields comparable to those obtained using palladium acetate, but with lower levels of isomeric by-products. Two representative procedures are reported here.

With CombiPhos POPd1: To a 50 mL reaction vessel were added, under an atmosphere of nitrogen, {PdCl[(t-butyl)$_2$P(O)][(t-butyl)$_2$P(OH)]}$_2$ (55 mg, 59 μmol), 3-bromo-5-isopropoxypyridine (5.25 g, 24.3 mmol), N-Boc-N-methyl-4-pentene-2-amine (6.20 g, 31.2 mmol), potassium carbonate (5.0 g, 36 mmol) and DMF (20 mL). The mixture was then stirred at 140° C. until the coupling reaction was complete (~12 h) as indicated by thin layer chromatography. The mixture was cooled to 25° C. and partitioned between water and dichloromethane. Concentration of the dichloromethane layer left an oil which was combined with 6 M hydrochloric acid (25 mL). This mixture was stirred and heated at 55° C. until the removal of the protecting group was complete (~1 h) as indicated by thin layer chromatography. Sodium hydroxide 50% (aq) was added slowly until the mixture was strongly basic (pH>11), and the mixture was extracted with dichloromethane. Concentration of the dichloromethane layer gave a viscous oil. Gas chromatographic analysis (mass spectrometric detection) indicated that the (2S)-N-methyl-5-[3-(5-isopropoxypyridin)yl]-4-penten-2-amine thus produced was 97% the 4E isomer.

With CombiPhos POPd2: To a 50 mL reaction vessel were added, under an atmosphere of nitrogen, [PdCl$_2$(t-butyl)$_2$P(OH)]$_2$ (33 mg, 49 μmol), 3-bromo-5-isopropoxypyridine (2.67 g, 12.4 mmol), N-Boc-N-methyl-4-pentene-2-amine (3.50 g, 17.6 mmol), potassium carbonate (4.0 g, 29 mmol) and DMF (15 mL). The mixture was then stirred at 140° C. until the coupling reaction was complete (~4 h) as indicated by thin layer chromatography. The mixture was cooled to 25° C. and diluted with water, and filtered through diatomaceous earth. The filtrate and a dichloromethane rinse of the filter cake were shaken together, and the dichloromethane layer was drawn off and concentrated. The resulting oil was combined with 6 M hydrochloric acid (40 mL) and stirred at 25° C. until the removal of the protecting group was complete (~3 h) as indicated by thin layer chromatography. Sodium hydroxide 50% (aq) was added slowly until the mixture was strongly basic (pH>11), and the mixture was extracted with dichloromethane. Concentration of the dichloromethane layer gave a viscous oil. Gas chromatographic analysis (mass spectrometric detection) indicated that the (2S)-N-methyl-5-[3-(5-isopropoxypyridin)yl]-4-penten-2-amine thus produced was 97% the 4E isomer.

We claim:

1. A process for the preparation of (2S)-(4E)-N-methyl-5-[3-(5-isopropoxypyridin)yl]-4-penten-2-amine comprising:
   a) preparing (2S)-N-(tert-butoxycarbonyl)-N-methyl-4-penten-2-amine by a process comprising:
      i) preparing 4-penten-2(R)-ol by a process comprising:
         A) adding vinylmagnesium chloride to a mixture of copper (I) chloride and lithium chloride, followed by the addition of (R)-propylene oxide, in a suitable solvent;
      ii) adding the resulting 4-penten-2-ol to a solution of 1.0 mole-equivalent, relative to propylene oxide, of p-toluenesulfonyl chloride in tetrahydrofuran;
      iii) adding the resulting (R)-4-penten-2-yl p-toluenesulfonate in tetrahydrofuran solution to 40% aqueous methylamine;
      iv) combining the resulting (S)-N-methyl-4-penten-2-amine solution with a mixture of di-tert-butyl dicarbonate in methyl tert-butyl ether; and
      v) adding N,N-dimethylaminoethylamine to the reaction mixture of N-methyl-4-penten-2-amine to N-(tert-butoxycarbonyl)-N-methyl-4-pentene-2-amine to form (2S)-N-(tert-butoxy)-N-methyl-4-penten-2-amine;
   b) mixing (2S)-N-(tert-butoxycarbonyl)-N-methyl-4-penten-2-amine (1 mole-equivalent) and 5-bromo-3-alkoxypyridine (1.1 mole-equivalents) with a palladium source (0.01 mole-equivalents), a phosphine ligand (0.24 mole-equivalents) and a base (1.5 mole-equivalents) in a suitable organic solvent under an atmosphere of nitrogen;
   c) adding water and heating the mixture to 90° C. for 15 to 25 h;
   d) cooling the mixture and adding water and an acid, followed by stirring at 0-70° C. for 3 to 8 h;
   e) separating the organic solvent and the acidic aqueous phase followed by washing the aqueous phase with an organic solvent;
   f) adjusting the pH in the aqueous phase by the addition of a base; and
   g) extracting the product into the organic phase followed by separation of the organic phase; and optionally
   h) treating the organic phase with a metal scavenger or charcoal to yield a (2S)-(4E)-N-methyl-5-[3-(5-alkoxypyridin)yl]-4-penten-2-amine.

2. A process for the preparation of (2S)-(4E)-N-methyl-5-[3-(5-isopropoxypyridin)yl]-4-penten-2-amine comprising:

a) preparing (S)-N-methyl-4-penten-2-amine dibenzoyl-L-(−)-tartaric acid by a process comprising:

adding a solution of L-(−)benzoyl-tartaric acid to a solution of (S)-N-methyl-4-penten-2-amine in an organic solvent, wherein the solution of L-(−)benzoyl-tartaric acid is 0.5 mole-equivalent relative to (S)-N-methyl-4-penten-2-amine;

b) mixing (S)-N-methyl-4-penten-2-amine di-benzoyl-L-(−)-tartaric acid (1 mole-equivalent) and a 5-bromo-3-alkoxypyridine (1.1 mole-equivalents) with a palladium source (0.01 mole-equivalents), a phosphine ligand (0.24 mole-equivalents) and a base (1.5 mole-equivalents) in a suitable organic solvent under an atmosphere of nitrogen;

c) adding water and heating the mixture to 90° C. for 15 to 25 h;

d) cooling the mixture and adding water and an acid, followed by stirring at 0-70° C. for 3 to 8 h;

e) separating the organic solvent and the acidic aqueous phase followed by washing the aqueous phase with an organic solvent;

f) adjusting the pH in the aqueous phase by the addition of a base; and g) extracting the product into the organic phase followed by separation of the organic phase; and optionally h) treating the organic phase with a metal scavenger or charcoal to yield (2S)-(4E)-N-methyl-5-[3-(5-alkoxypyridin)yl]-4-penten-2-amine.

3. A process according to claim 1, wherein the amounts used in step a) i) A) are 0.01 mole-equivalent copper (I) chloride and 0.02 mole-equivalent lithium chloride relative to propylene oxide.

4. A process according to claim 1, wherein the amount of vinylmagnesium chloride used in step a) i) A) is less than or equal to 1.0 mole-equivalent relative to propylene oxide.

5. A process according to claim 1, whereby the palladium-containing toluene phase is maintained under an atmosphere of nitrogen and by addition of (2S)-N-(tert-butoxycarbonyl)-N-methyl-4-penten-2-amine (1 mole-equivalent) and 5-bromo-3-alkoxypyridine (1.1 mole-equivalents) and base (1.5 mole-equivalents) followed by steps c) to g) or optionally h).

6. A process according to claim 1, wherein the acid used in step d) is hydrochloric acid.

7. A process according to claim 1, wherein the base used in step f) is an amine.

8. A process according to claim 1, wherein the ligand used in step b) is a mono or bis phosphine.

9. A process according to claim 1, wherein the palladium source used in step b) is a Pd(II) complex or a Pd(0) complex.

10. A compound N-methyl-4-penten-2-amine hemi-di-benzoyl-L-(−)-tartaric acid salt.

11. A process according to claim 2, whereby the palladium-containing toluene phase is maintained under an atmosphere of nitrogen and by addition of (2S)-N-(tert-butoxycarbonyl)-N-methyl-4-penten-2-amine (1 mole-equivalent) and 5-bromo-3-alkoxypyridine (1.1 mole-equivalents) and base (1.5 mole-equivalents) followed by steps c) to g) or optionally h).

12. A process according to claim 2, wherein the acid used in step d) is hydrochloric acid.

13. A process according to claim 2, wherein the base used in step f) is an amine.

14. A process according to claim 2, wherein the ligand used in step b) is a mono or bis phosphine.

15. A process according to claim 2, wherein the palladium source used in step b) is a Pd(II) complex or a Pd(0) complex.

* * * * *